(12) United States Patent
Gurova et al.

(10) Patent No.: US 8,835,447 B2
(45) Date of Patent: Sep. 16, 2014

(54) METHOD FOR TREATING ANDROGEN RECEPTOR POSITIVE CANCERS

(75) Inventors: Katerina Gurova, Orchard Park, NY (US); Natalya Narizhneva, West Seneca, NY (US)

(73) Assignees: Health Research Inc., Buffalo, NY (US); Panacela Labs, Inc., Buffalo, NY (US)

( * ) Notice: Subject to any disclaimer, the term of this patent is extended or adjusted under 35 U.S.C. 154(b) by 0 days.

(21) Appl. No.: 13/501,566

(22) PCT Filed: Oct. 25, 2010

(86) PCT No.: PCT/US2010/053916
§ 371 (c)(1),
(2), (4) Date: Jul. 2, 2012

(87) PCT Pub. No.: WO2011/050353
PCT Pub. Date: Apr. 28, 2011

(65) Prior Publication Data
US 2012/0264771 A1    Oct. 18, 2012

Related U.S. Application Data

(60) Provisional application No. 61/254,395, filed on Oct. 23, 2009.

(51) Int. Cl.
| | | |
|---|---|---|
| *A61K 31/517* | (2006.01) | |
| *A61K 31/40* | (2006.01) | |
| *A61K 31/427* | (2006.01) | |
| *A61K 31/47* | (2006.01) | |
| *A61K 31/167* | (2006.01) | |
| *A61K 31/426* | (2006.01) | |
| *A61K 31/496* | (2006.01) | |
| *A61K 31/4439* | (2006.01) | |
| *A61K 31/122* | (2006.01) | |
| *A61K 31/4184* | (2006.01) | |
| *A61K 31/4192* | (2006.01) | |
| *A61K 31/404* | (2006.01) | |
| *A61K 31/357* | (2006.01) | |

(52) U.S. Cl.
CPC ............ *A61K 31/404* (2013.01); *A61K 31/427* (2013.01); *A61K 31/47* (2013.01); *A61K 31/167* (2013.01); *A61K 31/426* (2013.01); *A61K 31/496* (2013.01); *A61K 31/4439* (2013.01); *A61K 31/122* (2013.01); *A61K 31/4184* (2013.01); *A61K 31/4192* (2013.01); *A61K 31/517* (2013.01); *A61K 31/357* (2013.01)
USPC ......................................... 514/268; 514/411

(58) Field of Classification Search
USPC .......................... 514/268, 411, 369; 435/7.23
See application file for complete search history.

(56) References Cited

U.S. PATENT DOCUMENTS

| | | |
|---|---|---|
| 4,224,326 A | 9/1980 | Matsumoto |
| 5,420,273 A | 5/1995 | Klaus et al. |
| 2006/0003966 A1 | 1/2006 | Arbiser |
| 2007/0254875 A1 | 11/2007 | Zhi et al. |
| 2007/0299102 A1 | 12/2007 | Felding et al. |
| 2009/0023710 A1 | 1/2009 | Vicker et al. |
| 2009/0023742 A1 | 1/2009 | Dhanak et al. |

FOREIGN PATENT DOCUMENTS

| | | |
|---|---|---|
| WO | 9614090 A1 | 5/1996 |
| WO | 2008051523 A2 | 5/2008 |

OTHER PUBLICATIONS

The Journal of Clinical Investigation 313(7); 2013.*
Tararova, Natalia, D. et al. Prostate Cancer Cells Tolerate a Narrow Range of Androgen Receptor Expression and Activity, PROSTATE, Oct. 12, 2007, vol. 67, No. 16, pp. 1801-1815.
Narizhneva, Natalya et al. Inhibition of Androgen Independent Prostate Cancer Cells by Small Molecules, Proceedings of the American Association for Cancer Research Annual Meeting, Apr. 12, 2008, vol. 49, pp. 308-309.

* cited by examiner

*Primary Examiner* — Shirley V Gembeh
(74) *Attorney, Agent, or Firm* — Hodgson Russ LLP

(57) ABSTRACT

Provided is a method of inhibiting growth of androgen receptor positive cancer cells. The method entails administering to an individual diagnosed with or suspected of having an androgen receptor positive cancer and administering to the individual a composition containing a compound that can inhibit the growth of the androgen receptor positive cancer.

9 Claims, 20 Drawing Sheets

CLASS XX (c85)

METHOD FOR TREATING ANDROGEN RECEPTOR POSITIVE CANCERS

This invention was made with government support under grant no. R42 CA 110400-01 2004-2005 awarded by the National Institutes of Health. The government has certain rights in the invention.

This application claims priority to U.S. Provisional application No. 61/254,395, filed on Oct. 23, 2009, the disclosure of which is incorporated herein by reference.

FIELD OF THE INVENTION

This invention relates generally to cancer therapy and more particularly to methods for treating cancers that involve androgen receptor positive cancer cells.

DESCRIPTION OF RELATED ART

Prostate cancer (PCa) is the most frequent neoplastic disease and the second leading cause of cancer-related deaths in men, claiming more than 30,000 men each year in the United States alone. PCa tumors are composed primarily of prostate luminal epithelial cells. Differentiation of prostate luminal epithelial cells is controlled in part by Androgen receptor (AR) driven expression of prostate-specific markers. AR controls survival of the cells through mechanisms that remain unclear. In addition to prostate cancer, AR is in involved in the etiology of other cancers, including breast cancers. AR belongs to the family of steroid receptors and functions as a transcription factor. In the absence of ligand, members of this family are unstable proteins that reside in the cytoplasm bound to Heat Shock Protein 90 (Hsp90). Upon binding of a steroid such as androgen to the ligand binding domain (LBD) of AR, AR is freed from Hsp90 and translocates to the nucleus. Androgen-bound AR in the nucleus activates transcription of genes with androgen responsive elements (ARE) in their promoters (Cato, A. C., et al. 1998. Trends Endocrinol Metab 9:150-154). In addition to its function as a transcriptional activator, AR is also capable of repressing transcription of some genes (Claessens, et al. 2001. *J Steroid Biochem Mol Biol* 76:23-30).

Depletion of androgens causes death of normal prostate luminal epithelial cells, which demonstrates the critical role of the AR pathway in their survival. Cancerous prostate cells continue to express AR and their survival also depends on the presence of androgens, which makes androgen deprivation the therapy of choice for patients with advanced PCa. Anti-androgen therapies, including use of the inhibitors flutamide and casodex, are usually effective initially, but rarely result in a complete cure. PCa relapse occurs in most of patients treated with such therapies, which leads to androgen-independent, chemotherapy-resistant tumors with poor prognosis. Thus, resistance to anti-androgen therapy is a major obstacle in successful treatment of PCa.

Analysis of the mechanisms of androgen-independence acquired by PCa during tumor progression indicates that loss of AR signalling is involved rarely (Balk, S. P. 2002. *Urology* 60:132-138; discussion 138-139). On the contrary, androgen-independent PCa is typically characterized by heightened AR activity due to expression of AR mutants that are ligand-independent (constitutively active) or responsive to non-androgen ligands (Chen, Y., et al. 2008. *Curr Opin Pharmacol* 8:440-448; Tilley, et al. 1996. Clin Cancer Res 2:277-285; Koivisto, et al. 1998 Am J Pathol 152:1-9; Marques, et al. 2005. Int J Cancer 117:221-229; Bohl, Cet al. 2005. J Biol Chem 280:37747-37754; Hara, T., et al. 2003. Cancer Res 63:149-153).

It was recently shown that unlike normal prostate stem cells, prostate "tumor initiating cells" or "cancer stem cells", a minor cell population believed to be the major source of self-renewing tumor cells, express functional AR (Vander Griend, et al. 2008. Cancer Res 68:9703-97111). This, together with the observed maintenance of AR activity in PCa tumors that have progressed to the stage of castration resistance, indicates that AR is a promising potential therapeutic target for both androgen-dependent and -independent PCa, as well as other AR positive cancer types. For example, breast epithelial cells are, in many regards, similar to prostate cells. As the survival of PC cells depend upon the androgen-stimulated activity AR, breast epithelial cells are similarly dependent upon the related estrogen (ER) and progesterone receptors (PR). The role of ER and PR in breast cancer (BC) and modulation of their function as a therapeutic approach has been the focus of studies for many years. However, AR is expressed at low levels in normal mammary cells and at different levels in a majority of BCs, including 50% of "triple negative" (ER-, PR-, Her2-) BCs, for which targeted therapy is not yet available. Although the effect of androgens on breast epithelial cells has been addressed in several studies, the role played by AR in BC remains unclear (Birrell, et al. (1995) J Steroid Biochem Mol Biol 52, 459-467; Brettes, et al. (2008) Bull Cancer 95, 495-502; Di Monaco, et al. (1995) Anticancer Res 15, 2581-2584). Thus, current treatment modalities are largely ineffective for AR positive cancers, and there is an ongoing need for new methods for therapy of AR positive cancer cells, including but not limited to PCa and breast cancer.

SUMMARY OF THE INVENTION

The present invention provides a method for inhibiting the growth of AR positive cancer cells in an individual. The method comprises administering to an individual diagnosed with or suspected of having AR positive cancer a composition comprising a compound capable of inhibiting the growth of or killing AR positive cancer cells. The AR positive cells can be any AR positive cancer cells. In various embodiments, the AR positive cancer cells are breast cancer, prostate cancer, hepatocellular carcinoma cells, cells of thyroid cancer, glyoblastoma, or astrocytoma.

Structures of compounds suitable for use in the invention are depicted in FIGS. 7, 8, 9, 10, 11. Specific examples of compounds depicted in FIGS. 7, 8, 9, 10, 11 are designated as c5, c6, c11, c52 and c85, respectively. Each of the compounds is was identified from a screen of the DiverSet Chemical Library purchased from Chembridge Chemical Corporation (San Diego, Calif.), and each compound is associated with a publicly available Chembridge identification (ID) number which can be used to identify specific compound structures. In various embodiments, In various embodiments, c5 (Chembridge ID 6099112), c6 (Chembridge ID 5652306), c11 (Chembridge ID 6005978), c52 (Chembridge ID 5582367) and c85 (Chembridge ID 6028717) can be used in the method of the invention.

In one embodiment, the method of the invention comprises administering to an individual diagnosed with or suspected of having AR positive cancer a composition comprising a compound selected from the compounds designated herein as c5, c6, c11, c52 and c85, and combinations thereof.

In one embodiment, the composition administered to the individual comprises c52.

In another embodiment, the invention provides a method for identifying whether an individual is a candidate for treatment with a composition comprising a compound capable of inhibiting the growth of or killing AR positive cancer cells. The method comprises obtaining a biological sample from the individual and determining whether the sample comprises androgen receptor positive cancer cells, wherein determining that the biological sample comprises androgen receptor positive cancer cells is indicative that the individual is a candidate for the treatment, and wherein determining that the biological sample does not comprise androgen receptor positive cancer cells is indicative that the individual is not a candidate for the treatment.

BRIEF DESCRIPTION OF THE FIGURES

FIG. 2A provides a graphical representation of data obtained by analyzing colony formation assays of the indicated cells treated with different chemicals for 7 days. FIG. 2B provides a graphical comparison of EC50 (inhibition of AR-dependent reporter in CWR22R cells) and IC50 (toxicity to CWR22R cells). FIG. 2C provides a graphical representation of data showing dose-dependent toxicity of several compounds for a panel of cell lines of different origins. Error bars in FIGS. 2A and C—standard deviation between triplicates within experiment; in FIG. 2B—confidence intervals of EC50 and 1050.

FIG. 1A is a photographic representation of Western blotting of lysates from CWR22R cells treated with 10 mM of the indicated hits for 36 hrs. AR antibody reveals the full length and DLBD forms of AR naturally present in these cells. GAPDH antibody was used to control for protein loading. FIG. 3B provides a graphical representation of data showing that, unlike parental CWR22R cells, a clone selected in the presence of c52 (c52R) is resistant to the effects of c52. AR protein expression in the c52R clone of CWR22R is not reduced by c52 treatment. Western blotting of parental and c52-resistant CWR22R cells with or without c52 treatment (10 µM for 36 hrs). FIG. 3C provides a graphical representation of data from analyzing cell viability by methylene blue staining 4 days after compound addition. Error bars—standard deviation between triplicates within experiment. FIG. 3D provides a graphical representation of data showing effects of the selected compounds on cell cycle distribution of CWR22R cells measured by propidium iodide staining of cellular DNA content by fluorescent activated cell sorting. Assay was done twice. Error bars—deviation between two measurements.

FIGS. 4A and 4B provide data comparing effects of two different shRNAs targeting AR (shAR5 and shAR6) and the AR mutant HD1-KRAB-AR122 on AR-dependent transcription and survival of AR-expressing PCa cells. FIG. 4B provides a graphical representation of data obtained from colony formation assays on CWR22R cells transfected with the indicated constructs and selected for puromycin resistance. Assay was done in duplicate. Error bars—deviation of the results between replicates.

FIG. 5A provides a graphical representation of data showing that ARE-Luc reporter activity in CWR22R cells can be induced by different steroids (DHT—dihydrotestosterone, Dex—dexamethasone, Ald—aldosterone), but depends on AR expression. siRNAs targeting AR or GAPDH (control) were transfected into CWR22R-ARE-Luc cells in SFM. The indicated concentrations of steroids were added to the transfected cells and luciferase activity was measured 24 h later. FIG. 4B provides a graphical representation of data showing effects of hit compounds on luciferase activity in MDA-MB-453-MMTV-Luc cells induced by DHT, Dex or Ald shown as % of DMSO control. X-axis—concentration of the hits in µM. Error bars show standard deviation between replicates within experiment.

FIG. 6A provides a graphical representation of data obtained from i.p. injection of the listed compounds or DMSO vehicle into nude mice carrying subcutaneous (s.c.) C4-2 tumors. Six daily injections were given starting when tumors were around 100 mm3 in size. There were 4-5 mice per group with two tumors per mouse. Asterisks (*) and number signs (#) are placed under the means of measurement in the c6 and c11 groups respectively which are statistically different from the control group by ANOVA test (>99%) B. C52 (9 mg/kg or 18 mg/kg) or DMSO vehicle was injected into the tail vein of nude mice carrying s.c. CWR22R tumors. Five daily injections were given starting when tumors were around 40 mm3 in size. There were 10 mice per group with one tumor per mouse. Asterisks (*) are placed under the means of measurement which are statistically different from the control group by ANOVA test (>99%). Error bars in both FIGS. 6A and B—standard deviation between the size of tumors within a given treatment group.

DESCRIPTION OF THE INVENTION

Figure 7:
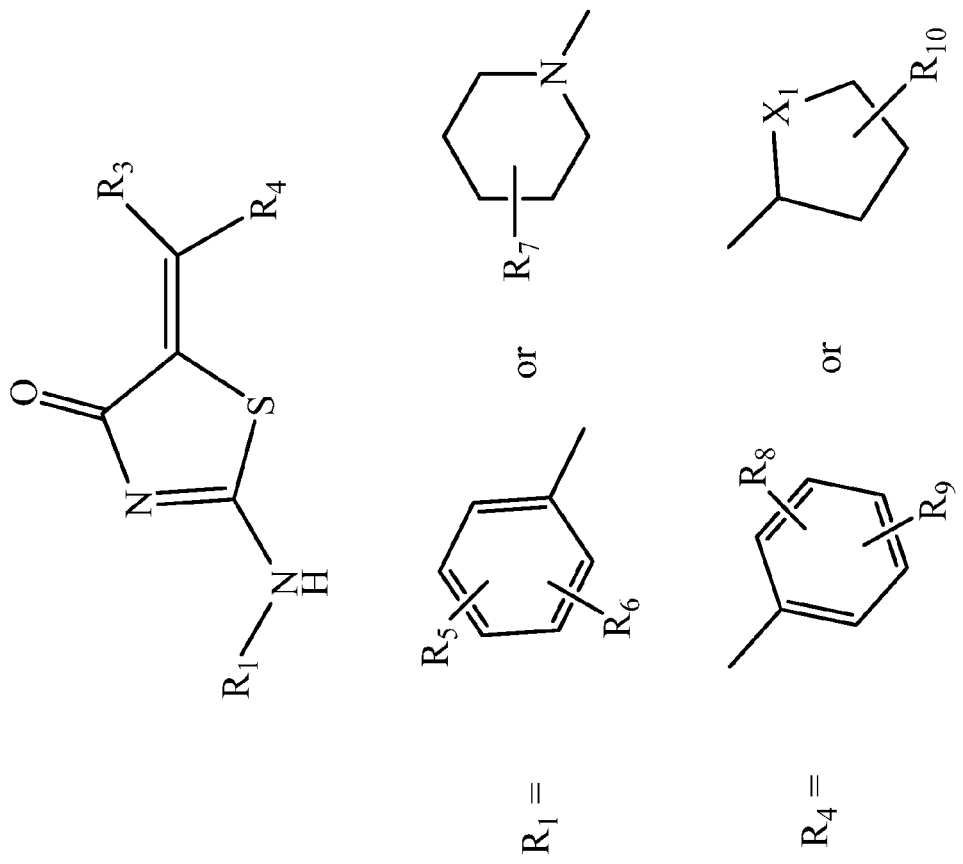
FIG. 7 provides structures of Class 1 compounds.
Figure 8:
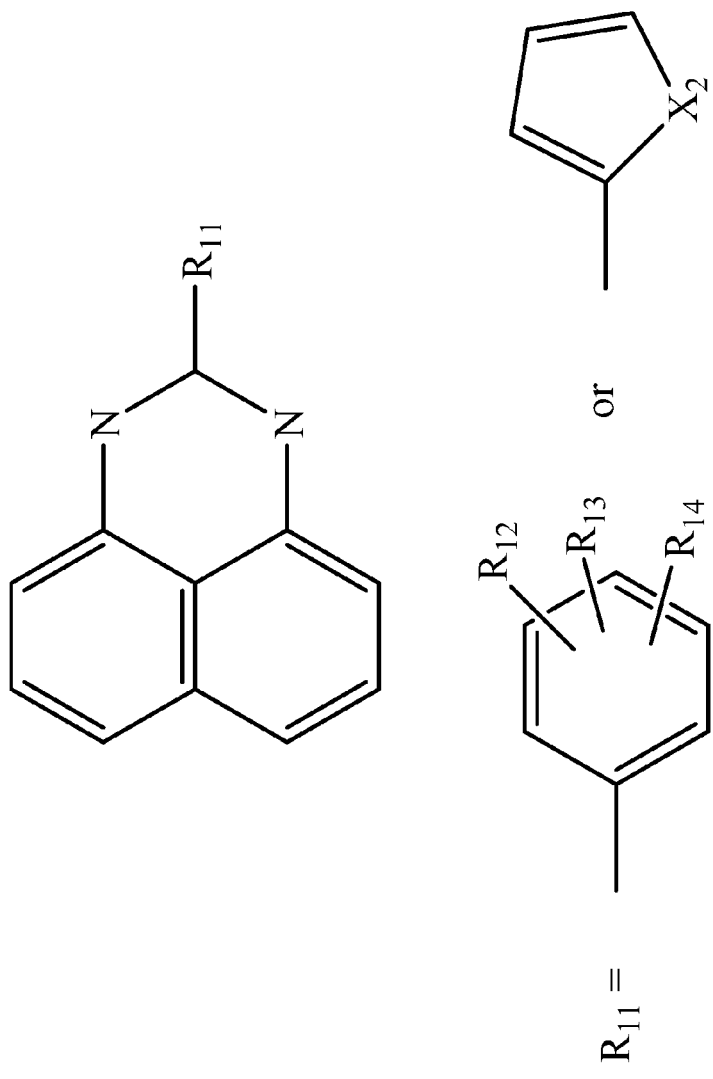
FIG. 8 provides structures of Class 3 compounds.
Figure 9:
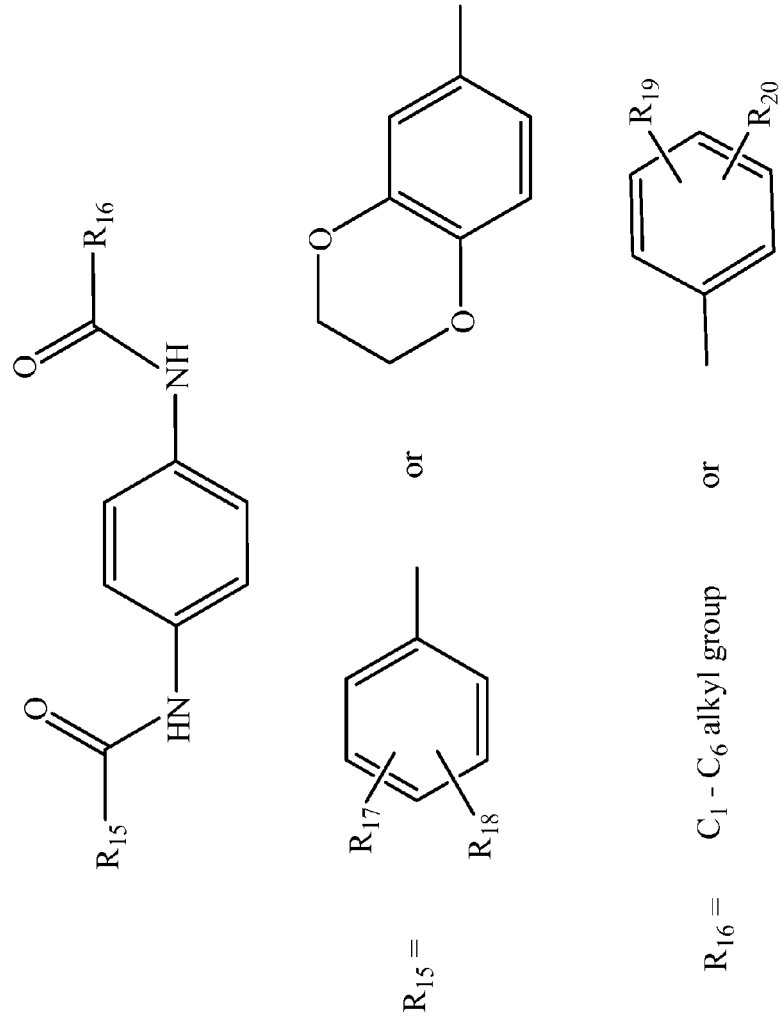
FIG. 9 provides structures of Class 6 compounds.
Figure 10:
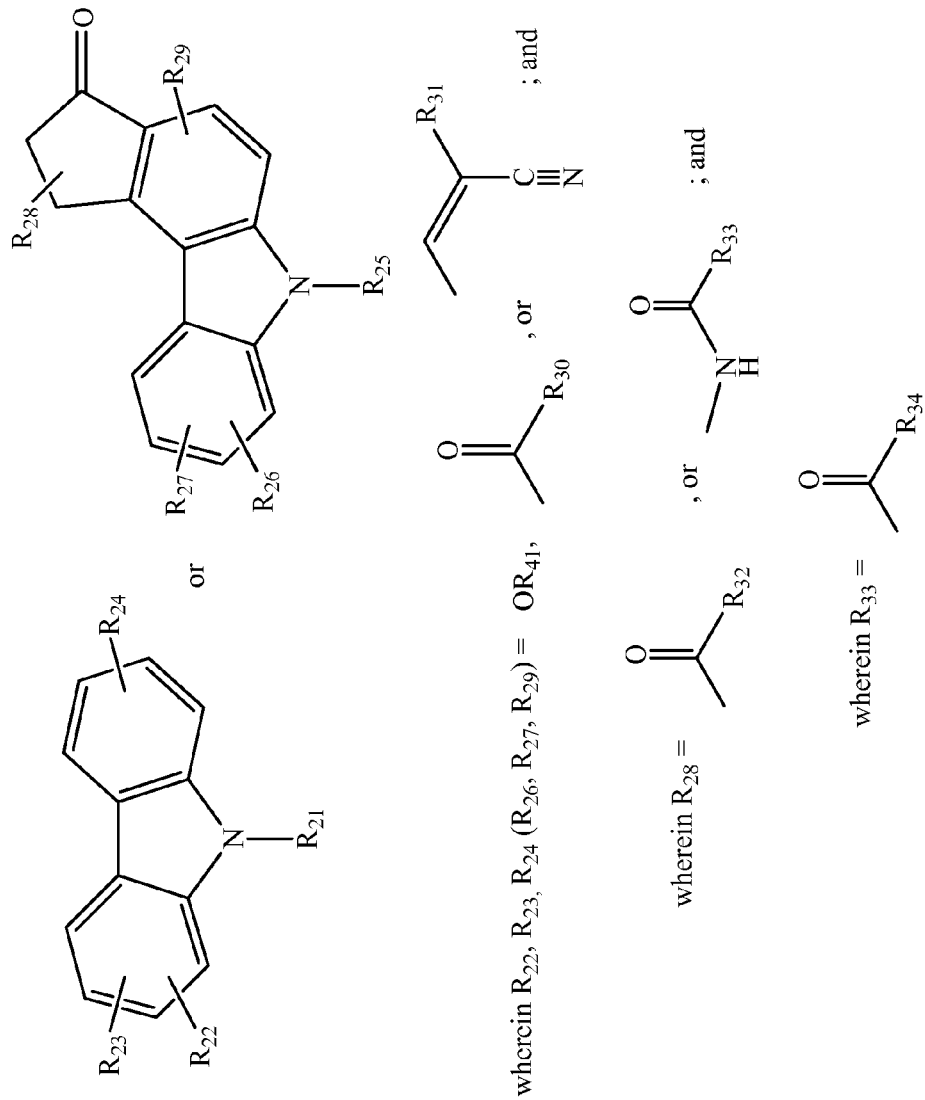
FIG. 10 provides structures of Class 54 compounds.
Figure 11:
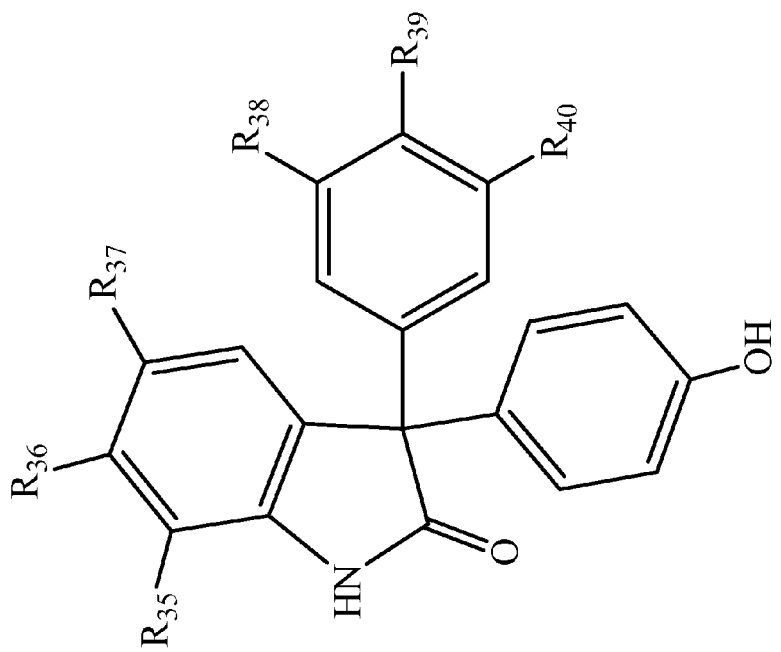
FIG. 11 provides structures of Class XX compounds.
Figure 12:
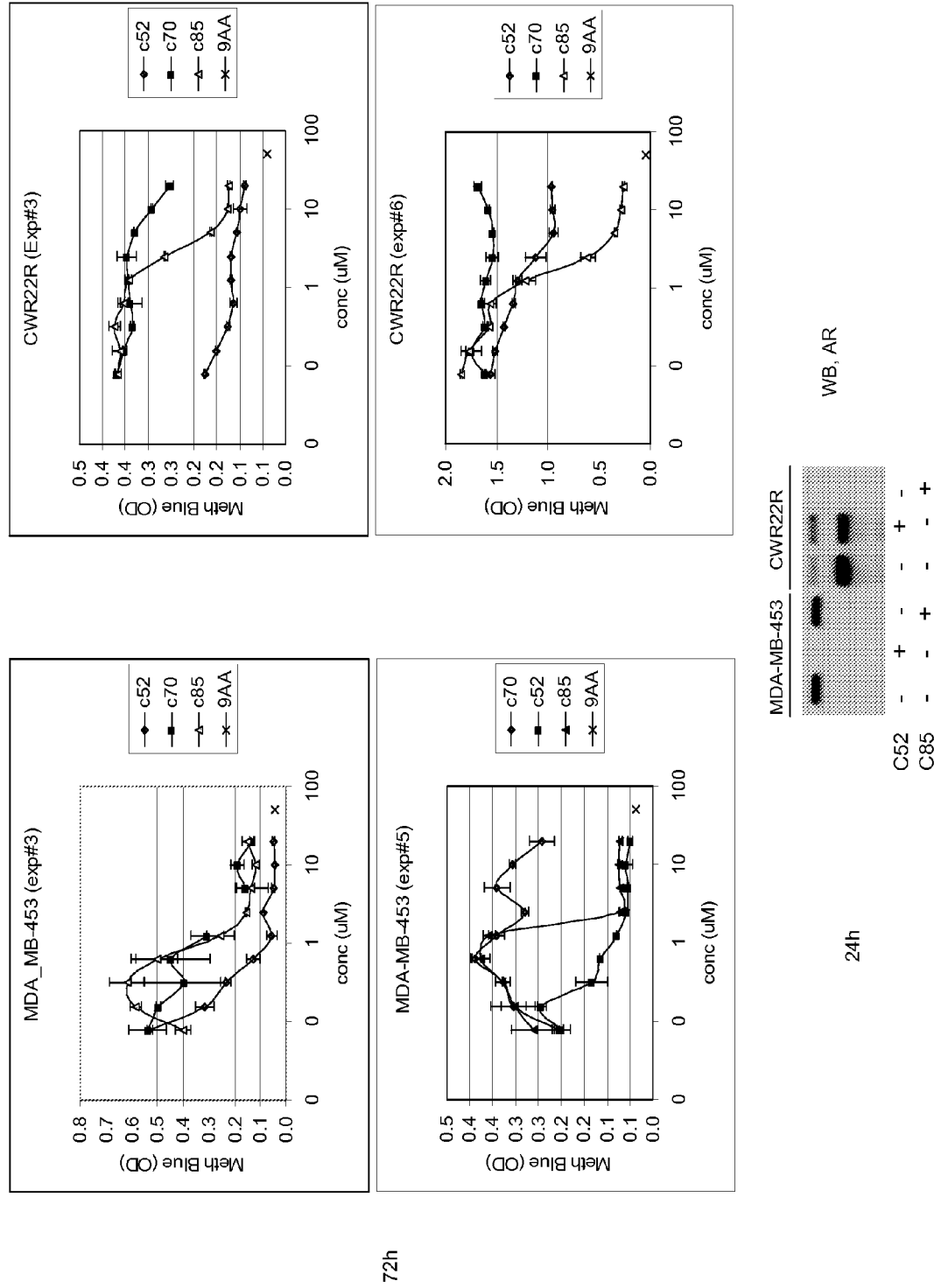
FIG. 12 provides a graphical representation of data obtained by analyzing cell death caused by various concentrations of compounds c52, c70 and c85 on different breast cancer and prostate cancer cells. 9AA is 9-amino agridine and is used as a positive control. Also shown is a Western blot (WB) showing the effects of the compounds on the expression of AR (AR).
Figure 13:
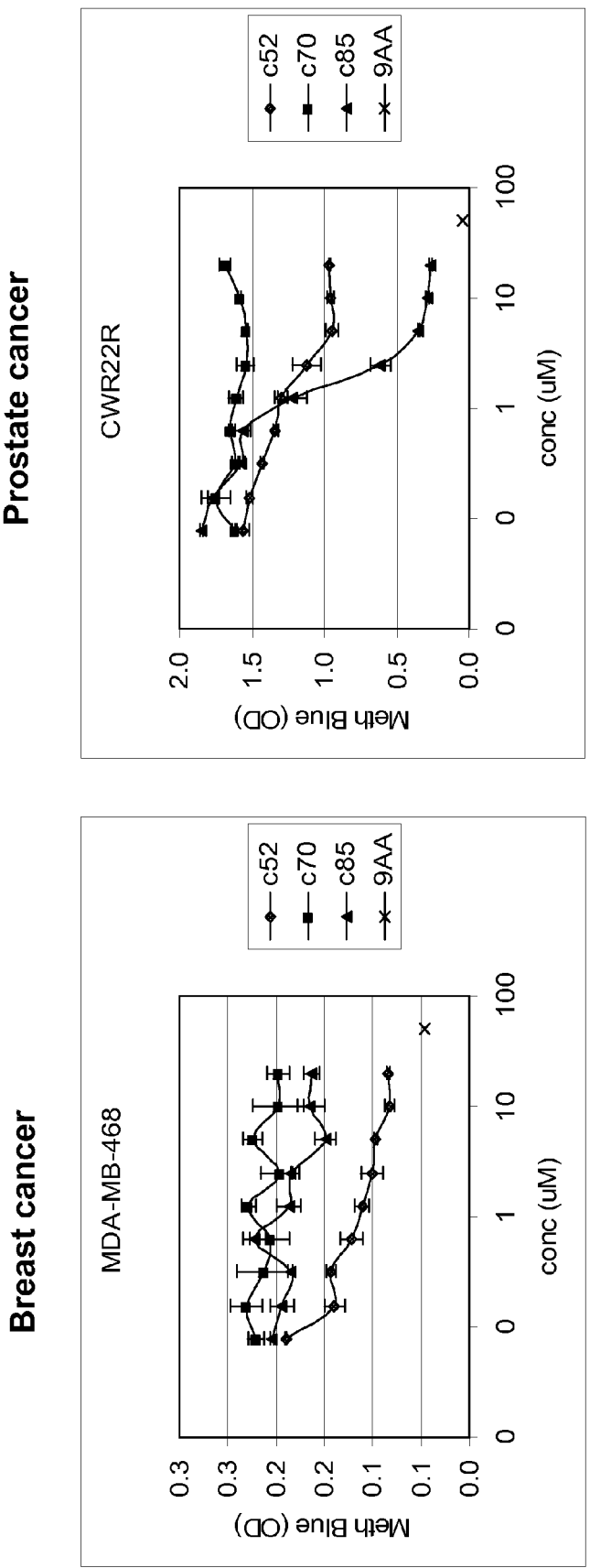
FIG. 13 provides a graphical representation of data obtained by analyzing cell survival in the presence of various concentrations of compounds c52, c70 and c85 on different breast cancer and prostate cancer cells.
Figure 14:
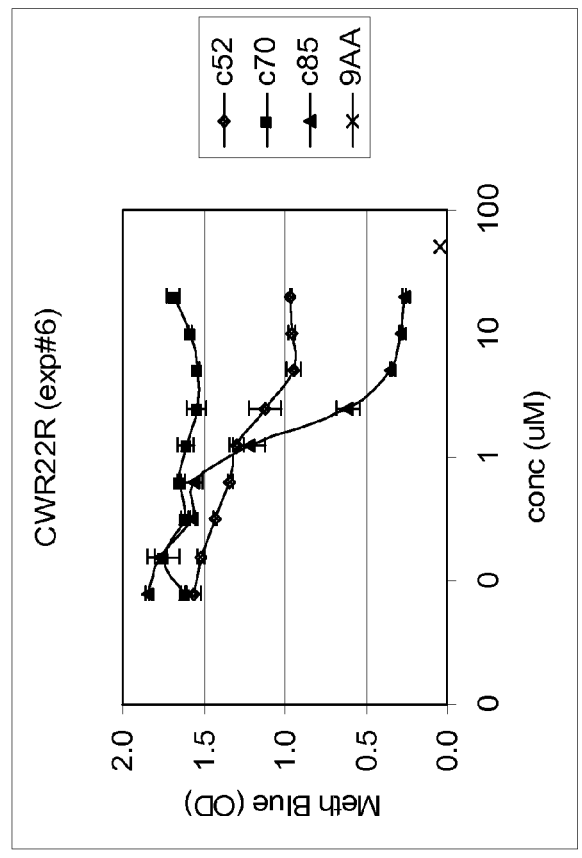
FIG. 14 provides a graphical representation of data obtained by analyzing cell cell survival in the presence of various concentrations of compounds c52, c70 and c85 on different breast cancer and prostate cancer cells. Also shown is a Western blot) showing the effects of the compounds on the expression of AR protein.
Figure 14:
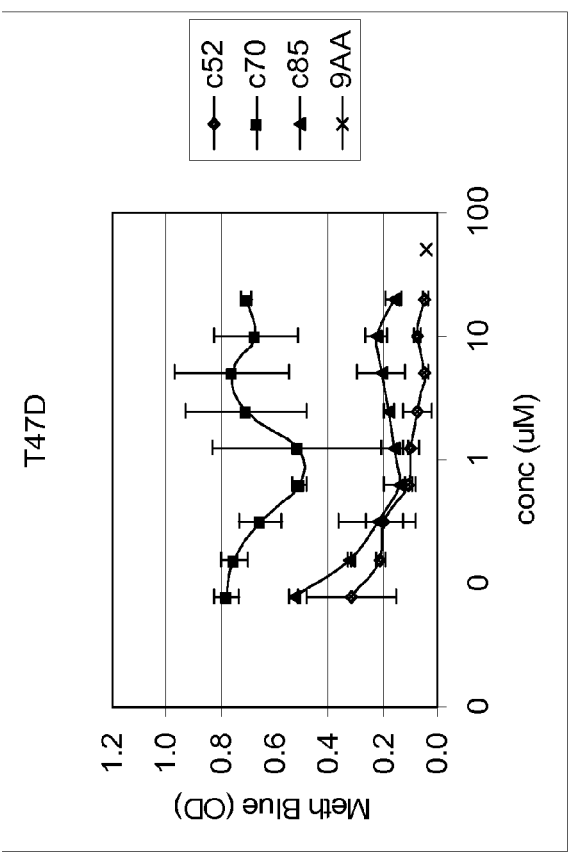
Figure 14:
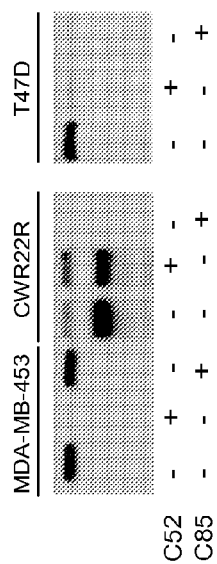
Figure 15:
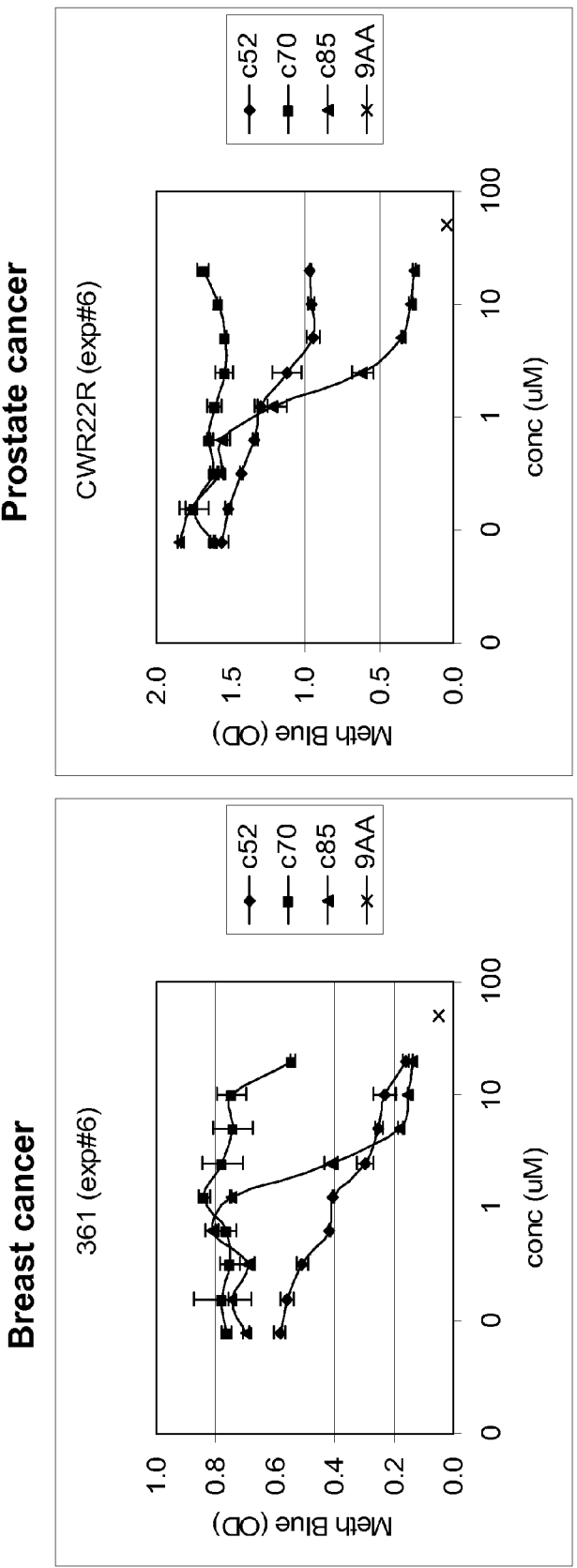
FIG. 15 provides a graphical representation of data obtained by analyzing cell cell survival in the presence of various concentrations of compounds c52, c70 and c85 on breast cancer and prostate cancer cells.
Figure 16:
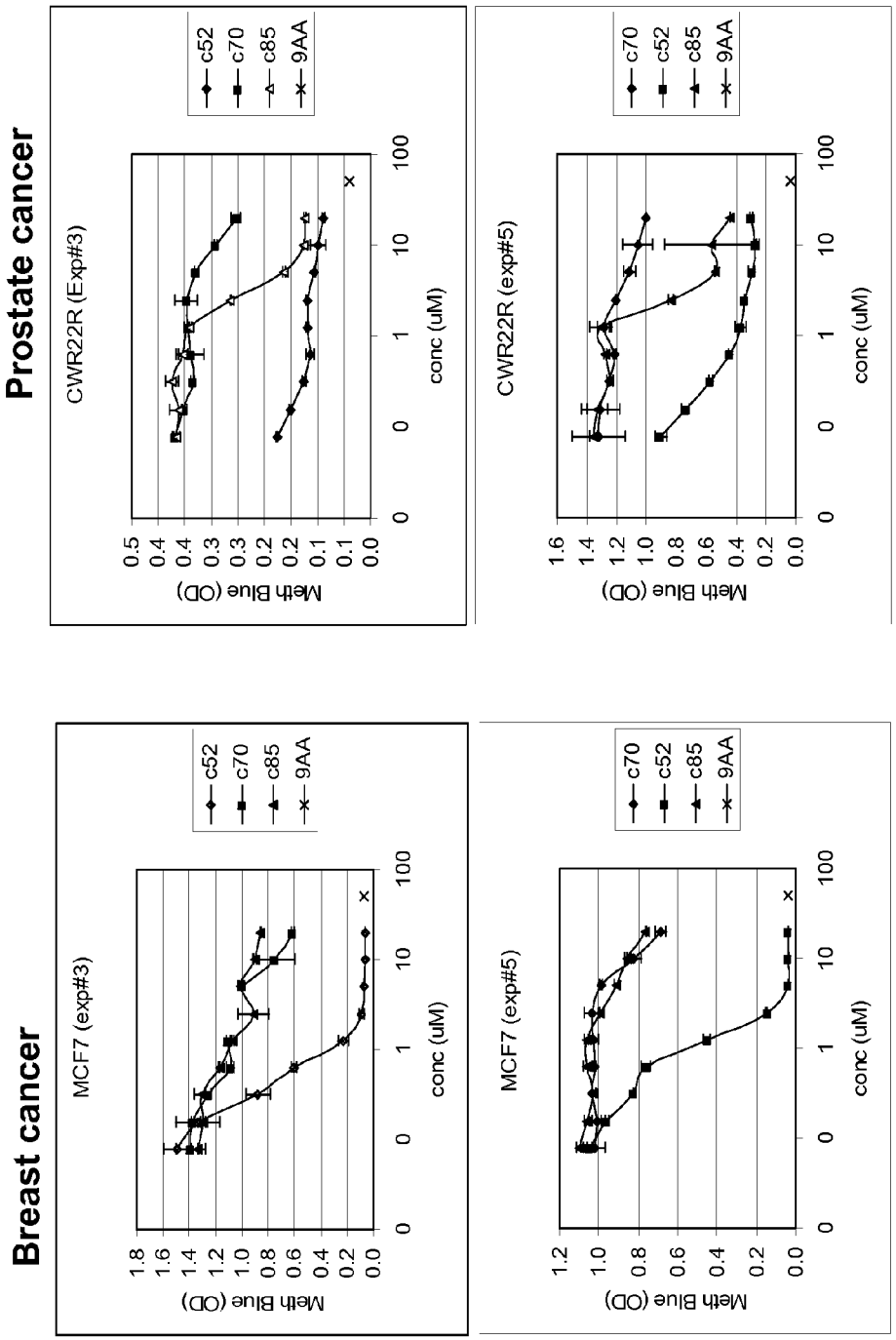
FIG. 16 provides a graphical representation of data obtained by analyzing cell death caused by various concentrations of compounds c52, c70 and c85 on breast cancer and prostate cancer cells.
Figure 17:
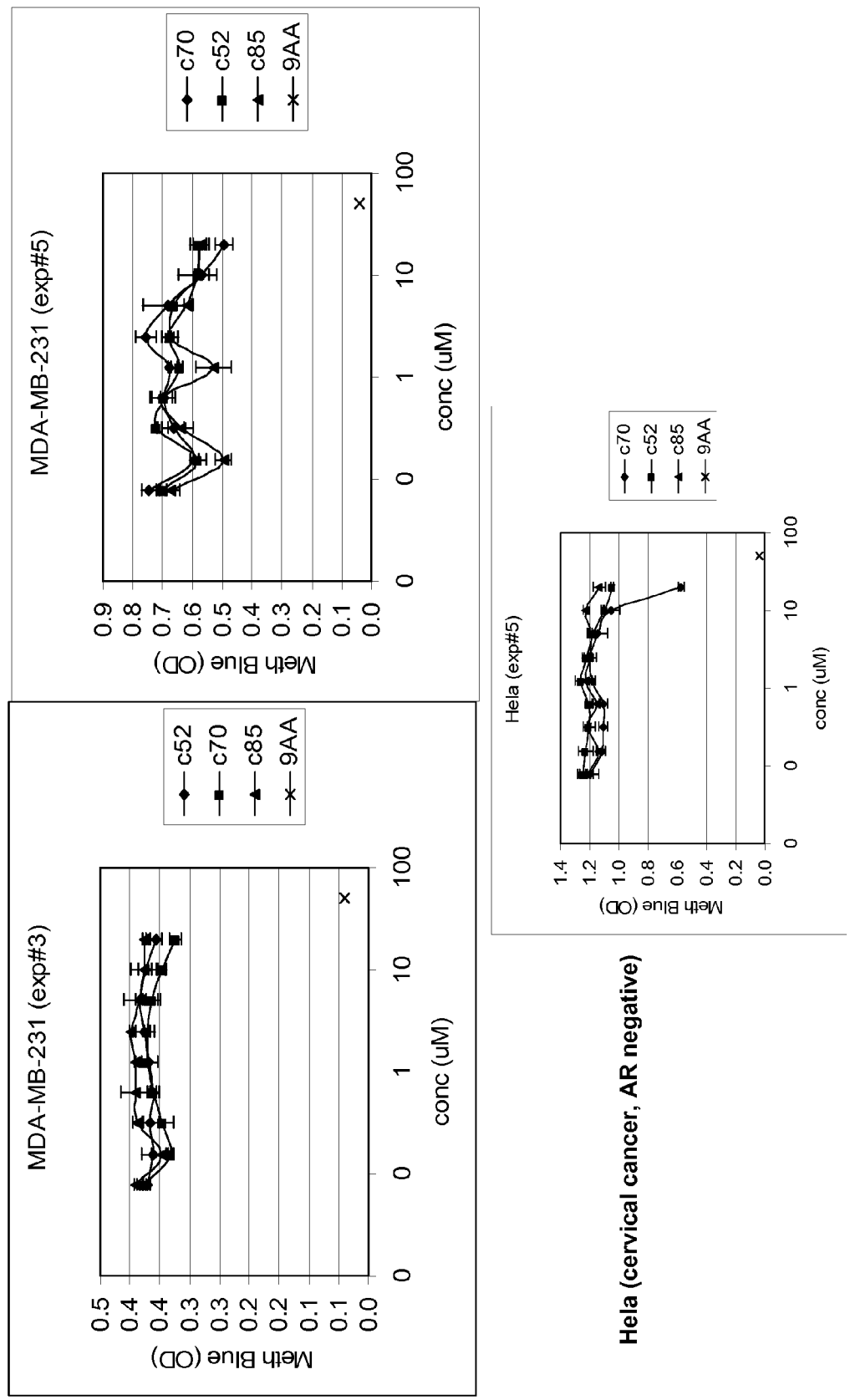
FIG. 17 provides a graphical representation of data obtained by analyzing cell cell survival in the presence of various concentrations of compounds c52, c70 and c85 on AR negative breast and cervical cancers.
Figure 18:
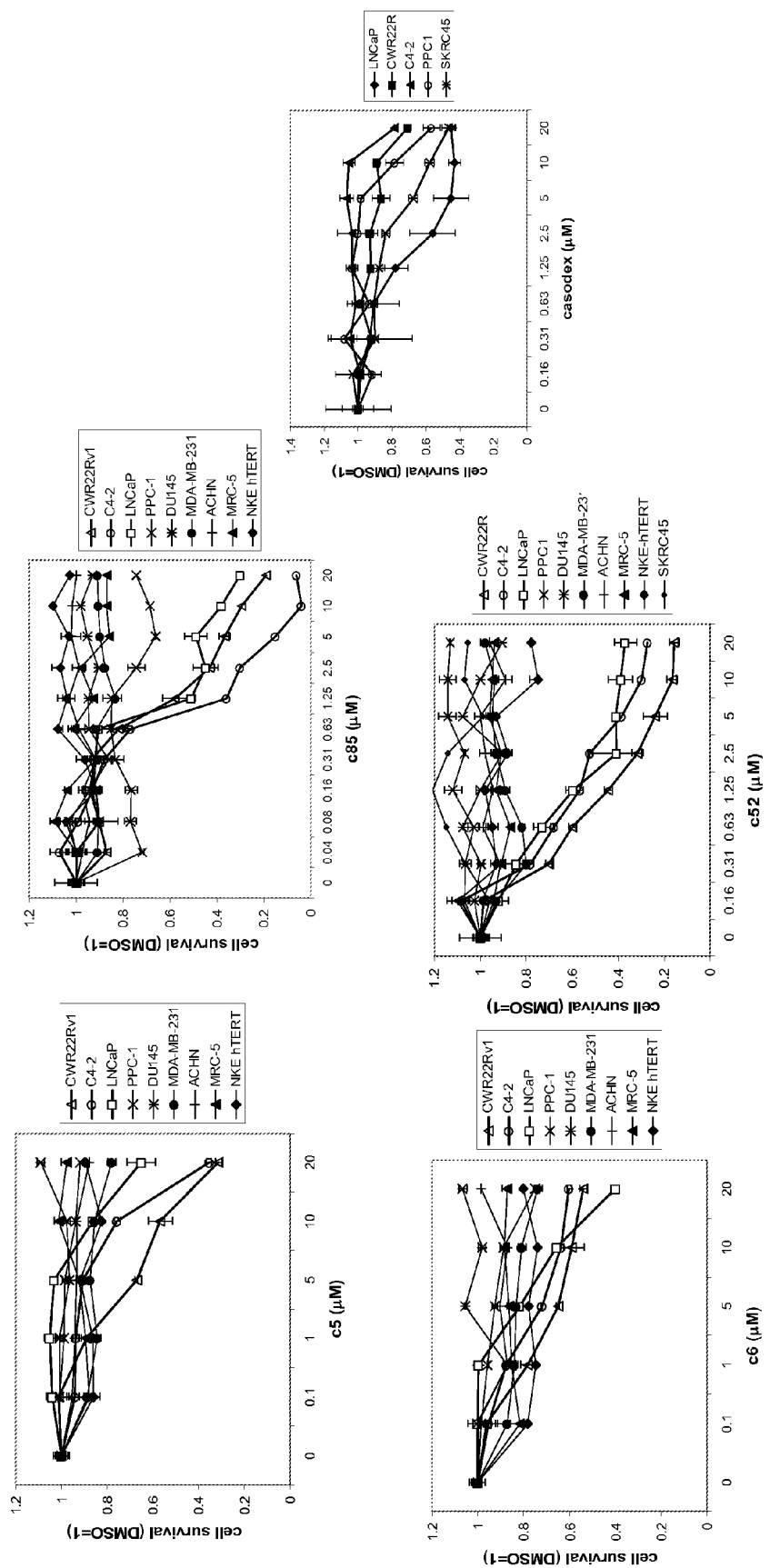
FIG. 18 provides a graphical representation of data obtained by analyzing the effects of varying concentrations of c5, c85, c6 and c52 on survival of multiple cells lines, including CWR22R, LNCaP, C4-2 (AR positive prostate cancer AR), PC3, DU145, PPC1 (AR negative prostate cancer), MDA-MB-231(AR negative breast cancer), ACHN, SK-RC45 (AR negative renal cell carcinoma), MRC5 (normal diploid fibroblasts) and NKE-hTERT (normal kidney epithelial fibroblasts)
Figure 19:
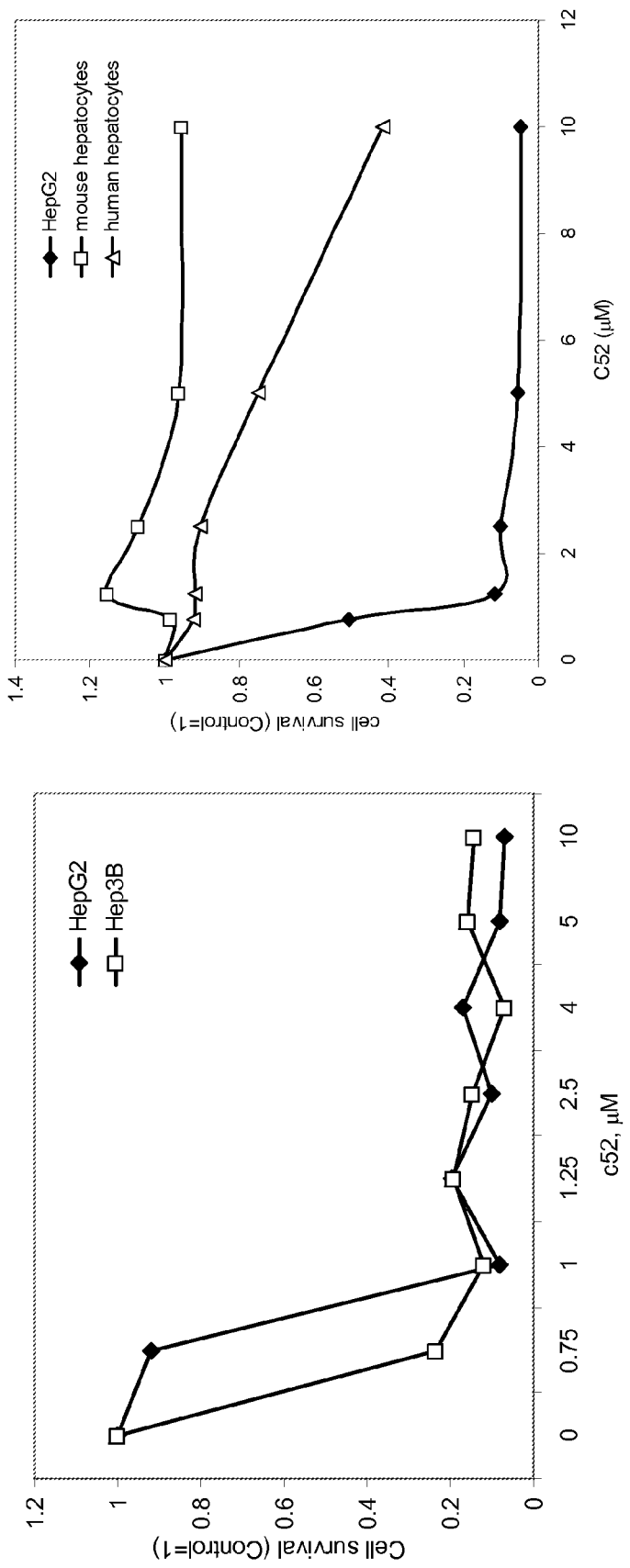
FIG. 19 provides a graphical representation of data obtained by analyzing varying concentrations of c52 on survival of HepG and Hep3B cells, and on mouse and human hepatocytes.
Figure 20:
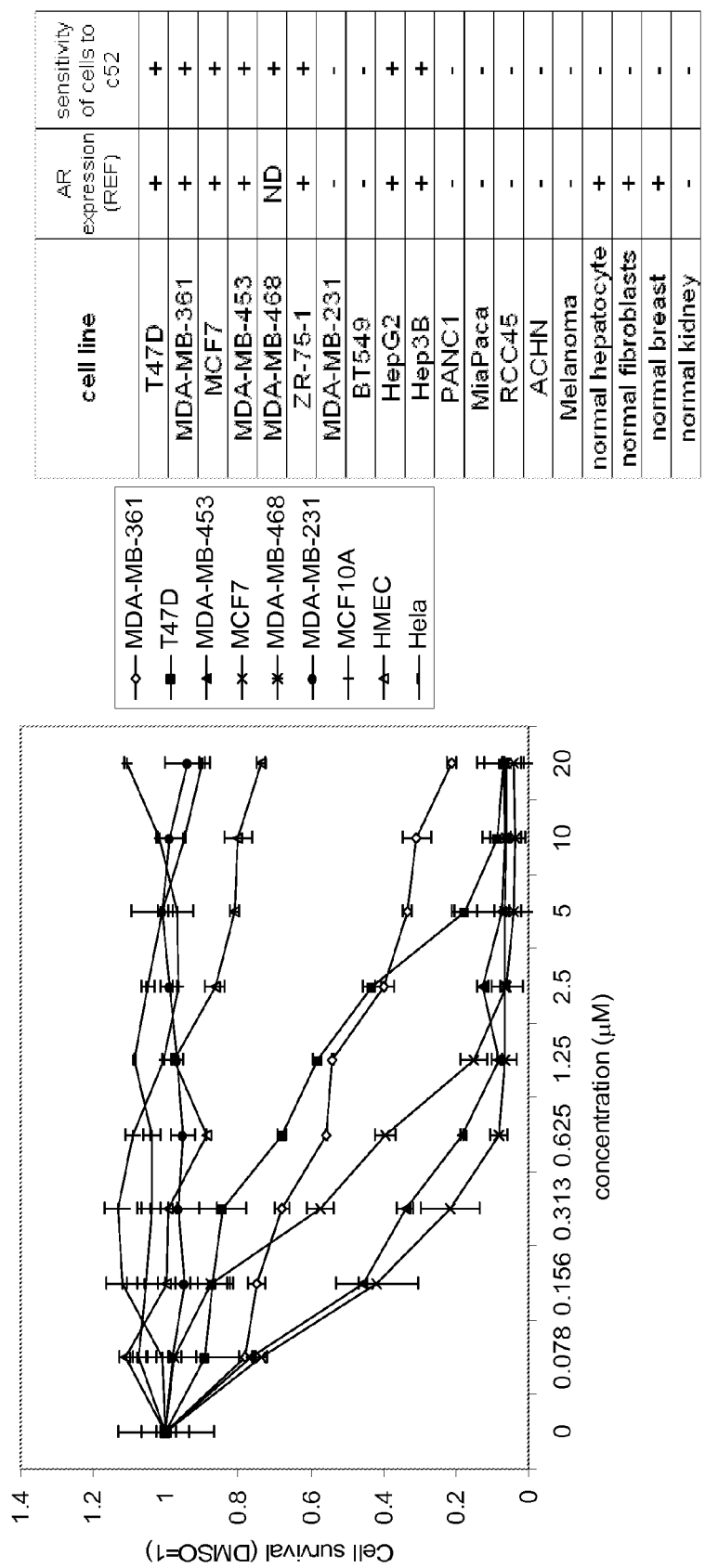
FIG. 20 provides a graphical representation of data obtained by analyzing sensitivity of different AR+ and AR- cells lines to varying concentrations of c52.

The present invention provides a method for inhibiting the growth of AR positive cancer cells in an individual. The method comprises administering to an individual diagnosed with or suspected of having AR positive cancer a composition comprising a compound capable of inhibiting the growth of or killing AR positive cancer cells. General structures of compounds suitable for use in the invention are depicted in FIGS. 7, 8, 9, 10, 11. The structures depicted in FIG. 7 are also referred to herein as Class 1. The structures depicted in FIG. 8 are also referred to herein as Class 3. The structures depicted in FIG. 9 are also referred to herein as Class 6. The structures depicted in FIG. 10 are also referred to as Class 54. The structures depicted in FIG. 11 are also referred to herein as Class XX.

Specific examples of compounds depicted in FIGS. 7, 8, 9, 10, 11 are designated as c5, c6, c11, c52 and c85, respectively. c5, c6, c11, c52 and c85 were identified as suitable for use in the method of the invention from 34,000 compounds present in the DiverSet Chemical Library purchased from Chembridge Chemical Corporation (San Diego, Calif.). Each of the compounds is associated with a publicly available Chembridge identification (ID) number and thus each structure can be accessed accordingly.

It will be recognized by those skilled in the art that the structures depicted in FIGS. 7-11 each include multiple compounds that are distinct from each other by way of alternative groups that can be present at the R positions. For example, for the class of compounds shown in FIG. 7, $R_5$, $R_6$ and $R_7$ are independently hydrogen; an alkyl group comprising 1 to 6 carbons; an aryl alkyl group, where the aryl moiety comprises 5 or 6 carbons and the alkyl moiety comprises 1 to 4 carbons (such as methylbenzene group); an alkyl ketone group, where the alkyl moiety comprises 1 to 4 carbons (such as an acetate group); halide (such as fluoride, chloride, bromide and iodide); or a hydroxyl group. $R_3$ is hydrogen or hydroxyl group. $R_8$, $R_9$ and $R_{10}$ are independently hydrogen; an alkyl group comprising 1 to 6 carbons; a halide (such as fluoride, chloride, bromide and iodide); or a nitro group. $X_1$ is an oxygen atom or sulfur atom.

For the class of compounds shown in FIG. 8, $R_{12}$, $R_{13}$ and $R_{14}$ are independently hydrogen; an alkyl group comprising 1 to 6 carbons; an alkyl ether group, where the alkyl moiety comprises 1 to 6 carbons (such as methyl ether or ethyl ether group); halide (such as fluoride, chloride, bromide and iodide); an amino group; a hydroxyl group; or a nitro group. $X_2$ is an oxygen atom or sulfur atom.

For the class of compounds shown in FIG. 9, $R_{17}$ and $R_{18}$ are independently hydrogen; an alkyl group comprising 1 to 6 carbons; or an alkyl ether group, where the alkyl moiety comprises 1 to 4 carbons (such as methyl ether or ethyl ether). $R_{19}$ and $R_{20}$ are independently hydrogen; an alkyl group comprising 1 to 6 carbons; or halide (such as fluoride, chloride, bromide and iodide).

For the class of compounds shown in FIG. 10, $R_{21}$ ($R_{25}$) is hydrogen; or an alkyl group comprising 1 to 6 carbons, which can optionally be substituted with one or more hydroxyl groups or cyano. $R_{22}$, $R_{23}$ and $R_{24}$ ($R_{26}$, $R_{27}$ and $R_{29}$) are independently hydrogen; an alkyl group comprising 1 to 6 carbons; an alkyl ketone group, where the alkyl moiety comprises 1 to 4 carbons and can optionally be substituted with one or more halides (such as an acetate group or a trifluroacetate group); an alkoxy group, wherein the alkyl moiety comprises 1 to 4 carbons and can optionally, be substituted with one or more halides; halide (such as fluoride, chloride, bromide and iodide); an alkyl sulfonamide, where the alkyl group comprises 1 to 4 carbons (such as a methylsulfonamide); or a hydroxyl group. $R_{30}$, $R_{31}$ and $R_{41}$ are independently hydrogen or an alkyl group comprising 1 to 6 carbons, which can optionally be substituted with one or more halides. $R_{32}$ is an alkyl group comprising 1 to 6 carbons, which can optionally be substituted with one or more halides (such as fluoride, chloride, bromide and iodide); or an amino group. $R_{33}$ and $R_{34}$ are independently an alkyl group comprising 1 to 6 carbons, which can optionally be substituted with one or more halides (such as fluoride, chloride, bromide and iodide); or an alkylcyclohexyl group, where the alkyl moiety comprises 1 to 4 carbons (such as a methylcyclohexyl group).

For the class of compounds shown in FIG. 11, $R_{35}$ is hydrogen; an alkyl group comprising 1 to 6 carbons, which can optionally be substituted with one or more halides (such as fluoride, chloride, bromide and iodide); or halide (such as fluoride, chloride, bromide and iodide). $R_{36}$ and $R_{37}$ are independently hydrogen; or an alkyl group comprising 1 to 6 carbons, which can optionally be substituted with one or more halides (such as fluoride, chloride, bromide and iodide). $R_{38}$ and $R_{39}$ are independently hydrogen; an alkyl group comprising 1 to 6 carbons, which can optionally be substituted with one or more halides (such as fluoride, chloride, bromide and iodide); or a hydroxyl group. $R_{40}$ is hydrogen or a hydroxyl group. Some structures presented herein do not depict hydrogen at certain positions. It would be understood by one having skill in the art that such structures include such hydrogen substituents.

Specific examples of compounds encompassed within the instant disclosure are designated c5, c6, c8, c11, c16, c17, c18, c47, c52, c55, c61, c66 and c73 (Chembrige ID No. 6443213). Specific structures with Chembridge ID numbers are shown below.

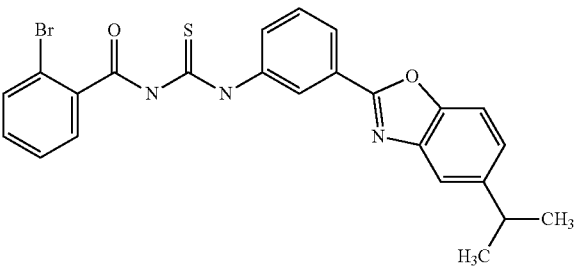

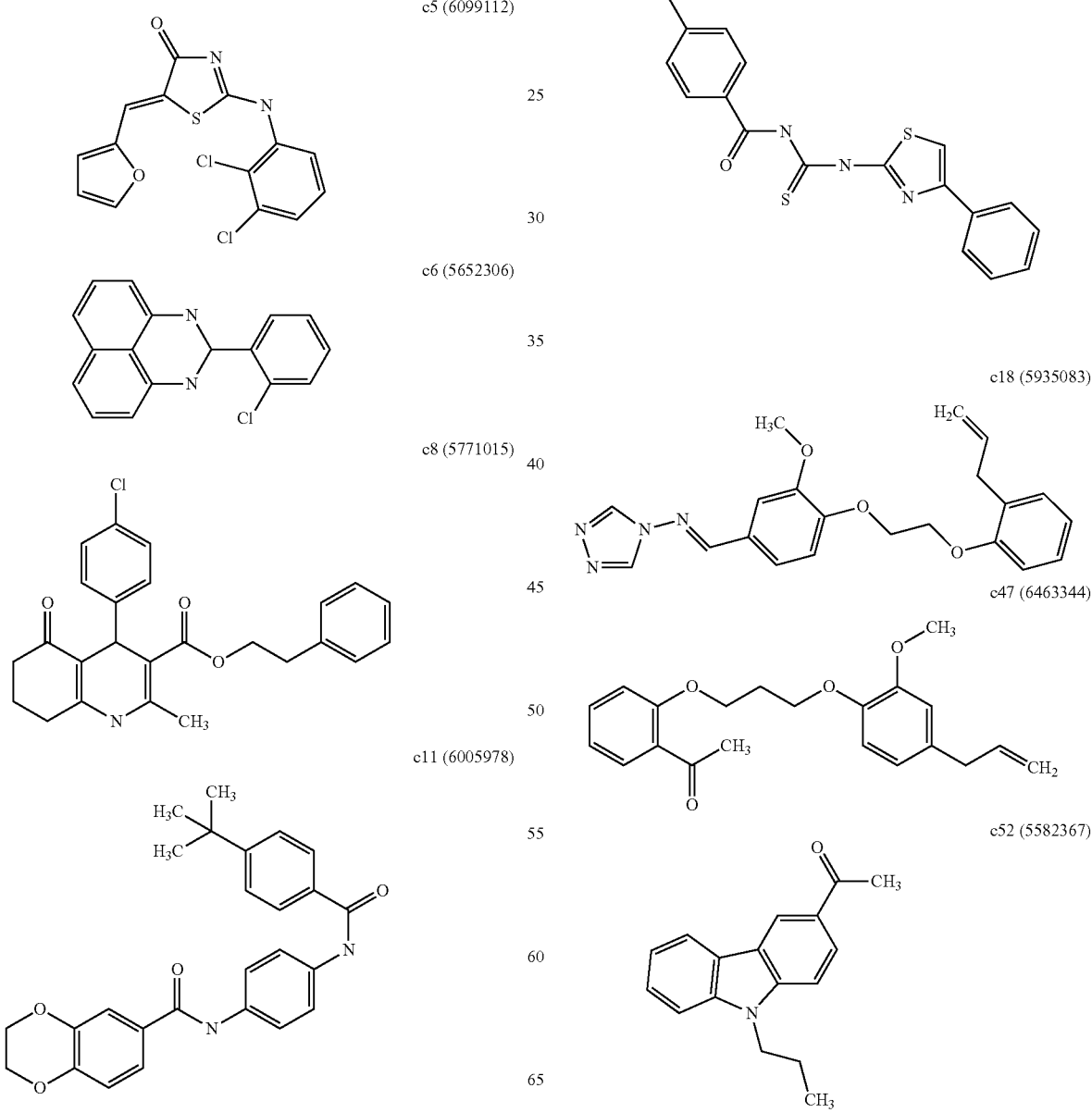

-continued c55 (6104475)

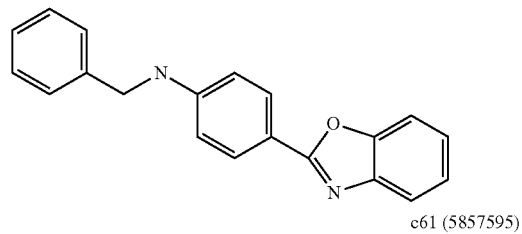

c61 (5857595)

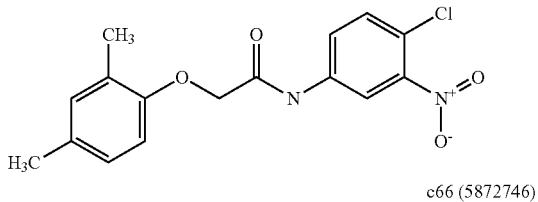

c66 (5872746)

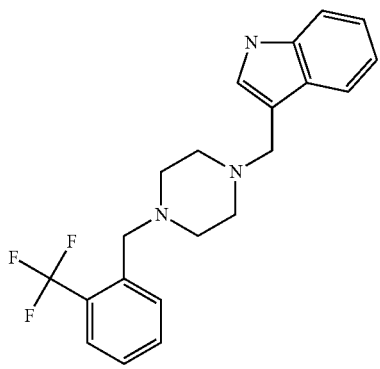

c85 (6028717)

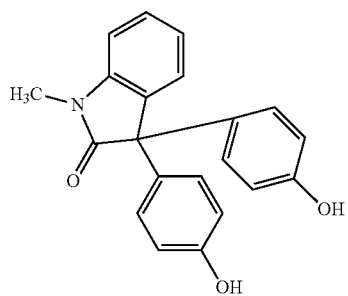

In one embodiment, the method of the invention comprises administering to an individual diagnosed with or suspected of having AR positive cancer a composition comprising a compound selected from the compounds designated herein as c5, c6, c11, c52 and c85, and combinations thereof.

In one embodiment, the composition administered to the individual comprises c52.

The AR positive cancer cells referred to herein are cancer cells that express a detectable amount of AR protein. "Androgen receptor" (and thus its abbreviation "AR") is a term well known to those skilled in the art and is used herein to refer to AR protein expressed by human cancer cells, including all isoforms and allelic variants of human AR protein.

In one embodiment, AR positive cancer cells, the growth of which can be inhibited in an individual by practicing the method of the invention, are cells that express AR that is specifically recognized by any type of anti-human AR antibody. Anti-human AR antibodies are commercially available.

In one embodiment, AR positive cancer cells, the growth of which can be inhibited in an individual by practicing the method of the invention, are cells that express AR that can be specifically recognized by the anti-human AR antibody available from BD PharMingen, San Diego, Calif., under catalog number #554225. In one embodiment, a detectable amount of AR protein is an amount of AR protein that can be detected by a Western blot.

In one embodiment, AR positive cancer cells are cells that express AR having the amino acid sequence for GenBank accession no. P10275, Sep. 1, 2009 entry, which is incorporated herein by reference. In alternative embodiments, AR positive cancer cells are cells that express AR having an amino acid sequence that is between 70%-99%, inclusive, and including all integers there between, homologous to the amino acid sequence provided for GenBank accession no. P10275, Sep. 1, 2009. The AR positive cells can by cancer cells that express such an AR having any of such sequences, wherein the AR is detectable by Western blot.

The AR positive cancer cells can be any type of cancer cells. In one embodiment, the cancer cells are prostate cancer cells. The prostate cancer cells may be androgen dependent or androgen independent.

In another embodiment, the AR positive cells are breast cancer cells. The breast cancer cells may be any type of breast cancer cells, provided they are AR positive. The breast cancer cells may be any of ER-, PR-, Her2-, or combinations thereof.

In another embodiment, the AR positive cells are hepatocellular carcinoma cells, cells of thyroid cancer, glyoblastoma, or astrocytoma.

The inhibition of growth of the AR positive cancer cells may be partial inhibition or complete inhibition. Eradication of some or all AR positive cancer cells from an individual is considered to be a type of inhibition of growth of the AR positive cancer cells.

In one embodiment, the invention comprises inhibiting the growth of cancer cells by contacting the cells with an effective amount of a composition comprising a compound having a structure depicted in FIGS. 7, 8, 9, 10, 11.

In one embodiment of the invention, an individual can be identified as a candidate for treatment with a composition comprising an effective amount of a compound selected from the group of compounds depicted in FIGS. 7, 8, 9, 10, 11. The individual can be identified as such a candidate by obtaining a biological sample of cancerous tissue from the individual and determining whether or not the cancerous tissue expresses AR. Determining the cancerous tissue expresses AR is indicative that the individual is a candidate for the treatment. Likewise, determining that the tissue does not express a detectable amount of AR is indicative that the individual is not a candidate for the treatment. Determining whether the cancerous tissue expresses AR can be performed using any suitable technique, such as immunological techniques. In one embodiment, the invention includes transforming AR in a biological sample obtained from the individual into an AR-antibody complex, and detecting the AR-antibody complex using an immunodiagnostic device.

In various embodiments, the invention further comprises fixing in a tangible medium the determination of whether or not the cancerous tissue expresses AR, and/or fixing a treatment recommendation for the individual in the tangible medium. The tangible medium can be any type of tangible medium, such as any type of digital medium, including but not limited to digitized files that can be stored on a computer, a DVD, a CD-ROM, or an electronic mail message. The tangible medium could be provided to a health care provider so as to develop a treatment protocol whereby a treatment regime for the individual that comprises performing the method of the invention is developed.

Compositions comprising the compounds for performing the method of the invention may be prepared by mixing with any suitable pharmaceutically acceptable carriers, excipients and/or stabilizers. Some examples of compositions suitable for mixing with the compounds can be found in: *Remington: The Science and Practice of Pharmacy* (2005) 21st Edition, Philadelphia, Pa. Lippincott Williams & Wilkins.

Compositions comprising the compounds described herein can be administered to an individual using any available method and route, including oral, parenteral, subcutaneous, intraperitoneal, intrapulmonary, intranasal and intracranial injections. Parenteral infusions include intramuscular, intravenous, intraarterial, intraperitoneal, and subcutaneous administration.

The method of the invention can be performed prior to, concurrently, or subsequent to conventional anti-cancer therapies, including but not limited to chemotherapies, surgical interventions, and radiation therapy.

It will be recognized by those of skill in the art that the form and character of the particular dosing regimen employed in the method of the invention will be dictated by the route of administration and other well-known variables, the sex and size of the individual, and the type and stage of the particular cancer being treated. Based on such criteria, one skilled in the art can determine an effective amount of a composition to administer to the individual.

In arriving at the present invention, we identified AR inhibitors that target aspects of AR function that are distinct from AR—ligand interaction. We achieved this by first identifying specific inhibitors of AR-dependent transcription in ligand-independent PCa cell lines. We selected those compounds demonstrating specific toxicity against AR-expressing PCa cell lines. Notably, not all inhibitors of AR-dependent transcription were toxic to androgen-independent PCa cell lines, which indicates that AR transcriptional function does not, on its own, control PCa cell survival. We tested the best AR inhibitors for in vivo anti-tumor activity in mouse xenograft models of PCa, and we analyzed the molecular mechanisms of AR inhibition by the most effective compounds. This led to the discovery that elimination of AR protein from cells has a different impact on cell survival than suppression of the transactivation function of AR, which indicates that AR controls prostate cell survival, and likely other types of AR positive cancer cells, such as breast cancer cells, as evidenced by data presented herein, through a transcription-independent mechanism, which is believed to be an important and previously unrecognized anticancer approach.

The following Example is meant to illustrate but not limit the present invention.

EXAMPLE 1

This Example provides a description of the materials and methods used to obtain the results presented herein.

Cell lines: LNCaP, DU145, MDA-MB-453-MMTV-Luc, HeLa, ACHN, MRC5 and HT1080 cells were obtained from ATCC. RCC45 and normal kidney epithelial cell (NKE) were described in Gurova, et al. 2004. Cancer Res 64:1951-1958). Immortalized NKE-hTERT cells were obtained by transduction of human telomerase subunit in pBabe-puro vector. CWR22R and C4-2 cells were provided by Dr. Warren Heston (Department of Cancer Biology, Cleveland Clinic). The pARE-Luc reporter construct and CWR22R-ARE-Luc reporter cells were described already (Tararova, N. et al. 2007. Prostate 67:1801-1815). Although the consensus DNA element bound by AR is also recognized by several other steroid receptors, the pARE-Luc reporter utilizes a region of the probasin promoter that is known as one of the most AR-specific promoter regions (Tararova, N. et al. 2007. Prostate 67:1801-18154).

All prostate cell lines and MDA-MB-453-MMTV-Luc were cultured in RPMI 1640 media supplemented with 10% FBS, 1 mM sodium pyruvate, 10 mM HEPES buffer, 55 nM β-mercaptoethanol and antibiotics. HeLa and HT1080 cells were maintained in DMEM media with 10% FBS and antibiotics. Phenol red-free media and charcoal-stripped serum (CSS) were used to generate steroid-free media (SFM). CSS was purchased from Biosource (Rockville, Md.).

Plasmids: The pTZV-wtAR and pTZV-ARΔLBD lentiviral expression constructs were obtained by subcloning of wild type full length (1-919 aa) AR or the AR fragment corresponding to the first 639 aa of human AR into the pTZV-CMV vector (Tararova, N. et al. 2007. Prostate 67:1801-1815). The pLPCPw-shAR lentiviral vector directing expression of shRNA against human AR was generated as described (Tararova, N. et al. 2007. Prostate 67:1801-18154). The shRNA sequence corresponding to the non-translated region of human AR was TGATCCTCATATGGCCCAG. pHD1-KRAB-AR122 was obtained from Dr. G. Jenster (Department of Urology, Josephine Nefkens Institute, Erasmus M C, Rotterdam, the Netherlands) and was already described (23). The pLV-CMV-Luc vector was kindly provided by Dr. Peter Chumakov (Department of Molecular Genetics, Cleveland Clinic).

Lentiviral transduction and siRNA transfection were performed as previously described and using conventional techniques (Gurova, et al. 2004. *Cancer Res* 64:1951-1958).

Chemicals: The 34,000 DiverSet Chemical Library (consisting of small polycyclic molecules of molecular weight around 500 Da) was purchased from Chembridge Chemical Corporation (San Diego, Calif.). DHT was obtained from Cleveland Clinic Pharmacy Department (Cleveland, Ohio). Aldosterone, dexamethasone, BSA, RNase A and propidium iodide were purchased from Sigma-Aldrich (St. Louis, Mo.). Casodex (bicalutamide) was purchased from TRC (Toronto, Canada).

Primary Chemical Screening: Chemicals from the DiverSet Library were applied to a monolayer of CW22R-ARE-Luc cells in 96-well plates at a final concentration of 20 µM. The next day, luciferase activity was read using BrightGlo Luciferase Assay System (Promega, Madison, Wis.) and the percentile of the reporter activity in chemical-treated cells was calculated (as compared to cells treated with DMSO taken as 100%). Compounds for which this parameter was 50% or lower were considered primary hits. The list of hits was compared with those obtained from other screenings of the same library which included inhibitors of reporters driven by promoters containing p53, NF-κb, or E-box binding elements and compounds toxic to HeLa, melanoma and neuroblastoma cells. AR-inhibitory hits that were also present on any of these other lists were excluded from further consideration. Non-specific inhibition of transcription/translation or luciferase activity was tested in HT1080 cells with the CMV-luc reporter and hit compounds active in this system were eliminated from further consideration.

Dose-dependent inhibition of reporter activity: CWR22R cells were plated at $5 \times 10^4$ cells per well in 96-well plates. Compounds were added in a dose range from 1 to 20000 nM in two-fold increments. Each dose was tested in duplicate. Controls were 0.1% DMSO and 15 µg/ml actinomycin D. Luciferase activity was measured 24 h after compound addition by Bright Glo assay (Promega, Madison, Wis.). The assay was run two times and the effective concentration of compound inhibiting reporter activity by 50% as compared to DMSO ($EC_{50}$) was calculated by the sigmoid approximation method using CalcuSyn software (Biosoft, Chembridge, UK). Confidence intervals were calculated for each sigmoid.

Cell Colony Assay: Cells were plated in 24-well plates at a density allowing 6-7 days of exponential growth before confluency. Medium and compound was replaced every 48 hours to minimize the effect of potential compound instability. After 7 days of incubation in the presence of compound, cells were fixed and stained with methylene blue, followed by extraction of the stain with 1% SDS and spectrophotometry at 650 nm. Each assay was run in triplicate and the difference between control and compound-treated wells was determined using Student's t-test.

Dose-dependent inhibition of cell growth: Cells were plated at $1 \times 10^3$ cells per well in 96-well plates. Compounds were added in a dose range from 1 to 20000 nM in two-fold increments. Each dose was tested in triplicate. Controls were 0.1% DMSO (no effect on cell viability) and 50 µM 9-aminoacridine (complete cell death). Cells were incubated for 6 days and then fixed and stained with methylene blue, followed by extraction of the stain with 1% SDS and spectrophotometry at 650 nm. The assay was run two times and, based on the results, the inhibitory concentration of compound suppressing cell growth by 50% as compared to DMSO ($IC_{50}$) was calculated by the sigmoid approximation method using CalcuSyn software (Biosoft, Chembridge, UK). Confidence intervals were calculated for each sigmoid.

Selection of compound-resistant variants of CWR22R cells was done by incubation of $10^7$ cells for 3 days in the presence of $10 \times IC_{50}$ of a compound. Then cells were kept in drug-free medium until they reached a pre-confluent level. The procedure was repeated several times until no dead cells were observed in the presence of a compound.

PSA protein levels in conditioned media were determined after incubation of cells with or without 10 µM test compound for 72 h using "Human PSA ELISA Kit" from Antigenix America (Huntington, N.Y.).

Western blot analysis. Cells were lysed in Cell Culture Lysis Reagent (Promega, Madison, Wis.). Total protein concentration was determined using Dc Protein Assay (BioRad, Hercules, Calif.). Western blotting was performed using pre-cast 4-12% SDS Novex gels (Invitrogen) and PVDF membrane (Pharmacia BioTech). The following antibodies were used: against AR (BD PharMingen, San Diego, Calif.; #554225, 1 µg/ml); against GAPDH as a loading control (Santa Cruz Biotechnology Inc, Santa Cruz, Calif.).

Analysis of cell cycle distribution was based on staining of DNA content by propidium iodide. $10^5$ cells were removed from culture dishes using trypsin, washed with PBS and resuspended in 300 µl 3% BSA in PBS, followed by addition of 5 µl 70% ethanol. Cells were kept at $-20°$ C. for several hours and then stained with 10 µg/ml propidium iodide in the presence of 30 µg/ml RNase A for 2 hrs at 37° C. DNA content was assessed using a FACS Calibur instrument and CellQuest software (Becton Dickinson, Franklin Lakes, N.J.).

Testing of compound safety in mice was done according to an IACUC-approved protocol. The experiment was performed using outbred 8 week old NIH Swiss male mice from Harlan (Indianapolis, Ind.), 4 mice per group. $IC_{50}$ concentrations were used to calculate in vivo doses based on mouse weight ($IC_{50}$ in vivo dose equivalent in mg/kg=$IC_{50}$ in mg/ml×1000, based on the assumption that 1 g of mouse tissues have an approximate volume of 1 ml). The compounds were injected intraperitoneally (i.p.) in 25% DMSO-75% PBS starting from $20 \times IC_{50}$ equivalent of in vitro cytotoxic dose of compounds. The mice were observed for three days before each of two subsequent injections of $50 \times IC_{50}$ (dose 2) and $100 \times IC_{50}$ (dose 3). The control group of mice received 3 injections of 25% DMSO-75% PBS in intervals of three days. Blood biochemistry analysis was performed by BioReliance (Rockville, Md.).

Testing of the anti-tumor effect of compounds in mice was done according to an IACUC-approved protocol in 8 week old male athymic nude mice from Harlan (Indianapolis, Ind.). For the C4-2 xenograft model, $10^6$ C4-2 cells were injected subcutaneously (s.c.) in 2 sites of each mouse in 50% matrigel (BD Biosciences, Bradford, Mass.) in PBS. Upon development of visible tumors, they were measured using digital caliper. Tumor volume was calculated according to the formula: Volume=Length×Width/2. Mice were injected with compounds i.p. daily for 6 days starting on the day when at least one tumor per mouse reached 100 mm³ in size. Five mice per group were used. For the CWR22R xenograft model, CWR22R cells were inoculated ($10^5$ cells per inoculum) in 50% matrigel, one site per mouse. Treatment was started when the tumor grew to a size of at least 25 mm³. Compounds were diluted in captisol (CyDex, Lenexa, Kans.) and delivered intravenously (to reduce "first pass" liver effect) once a day for 5 days. Ten mice per group were used. Mice were monitored daily and tumors were measured every other day. Mice were euthanized according to institutional regulations when the size of tumor reached 1000 mm³. Comparison of the tumor growth in control and treated mice was done using ANOVA test.

EXAMPLE 2

This Example provides a description of the identification of compounds suitable for use in the method of the invention.

We screened a library of small molecules to identify inhibitors of AR. We selected a cell-based readout approach for a number of reasons, including (i) we wanted to broaden the potential target from just the AR protein itself to the entire AR signaling pathway, which is not possible with an in vitro biochemical assay; (ii) it is not clear what function/domain/binding site of AR is responsible for controlling cell survival; and (iii) the crystal structure of full length AR has not been resolved yet. Due to the latter two facts, a rational design approach is not possible.

Figure 1:
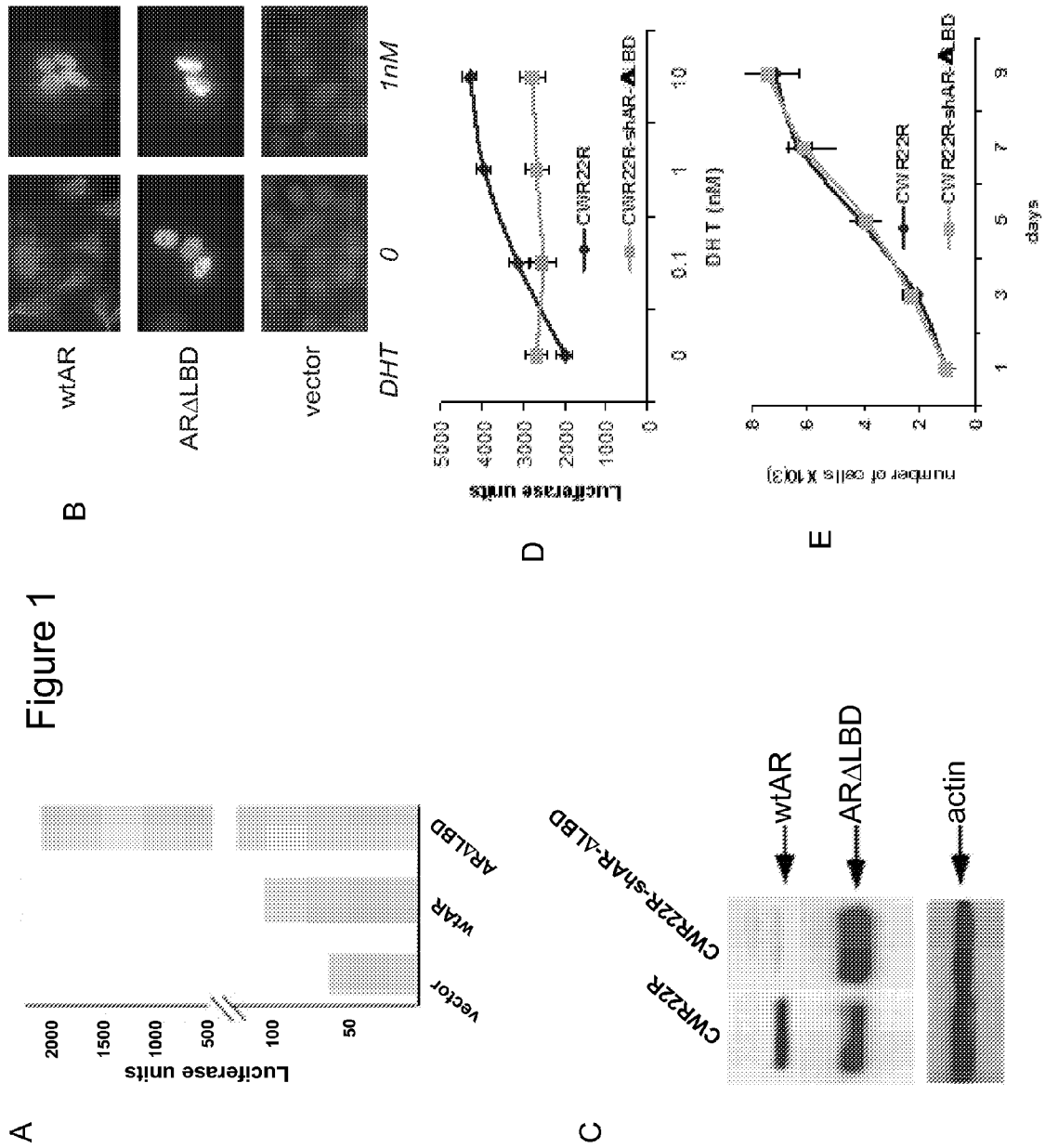
FIG. 1A provides a graphical representation of date showing that ARDLBD is transcriptionally active in serum-free media (SFM). HeLa cells were transfected in SFM with the AR-dependent reporter construct pARE-Luc and wild type (wt) AR, ARDLBD or negative control (empty vector) expression constructs. Luciferase activity was measured 24 hrs post-transfection.
FIG. 1B provides a photographic representations showing that ARDLBD has constant nuclear localization. HeLa cells transfected in SFM as in (A) were left untreated or treated with 1 nM dihydrotestosterone (DHT) for 24 hrs followed by immunofluorescent staining with anti-AR antibody. C-E. Substitution of the endogenous AR in CWR22R cells with ectopic ARDLBD by combined lentiviral transduction of shRNA targeting the untranslated region of the endogenous AR transcript and an ARDLBD expression construct.
FIG. 1C provides a photographic representation of results obtained by Western blotting of cell lysates prepared with or without transduction. Blots were probed with anti-AR and anti-actin antibodies.
FIG. 1D provides a graphical representation of data obtained from AR-dependent reporter assay (pARE-Luc) in original and transduced cells grown in SFM with addition of different concentrations of DHT.
FIG. 1E provides a graphical representation of data obtained from measuring growth rate (cell counts) of original and transduced cells in regular serum-containing medium. The assays shown in FIG. 1D and FIG. 1E were performed in triplicate. Error bars indicate standard deviation.

To increase the likelihood of identifying new types of AR inhibitors that act through mechanisms distinct from AR-ligand interaction, we selected the most androgen-independent cells from several available cultured cell lines, CWR22R, to use in the library screening. Proliferation of these cells is not affected by the absence of androgens and AR transcriptional activity is decreased minimally (compared to other PCa cell lines) as a result of androgen ablation. Another important feature of this cell line is that it expresses a truncated mutant of AR lacking the LBD (ARΔLBD Cancer Res 62:6606-6614). More than 50% of the AR protein present in CWR22R cells is the ARΔLBD form, while the remainder is full length with LBD mutations. Using cells in which much of the AR activity is due to a mutant lacking the LBD increased the chances of isolating small molecule inhibitors that act through mechanisms other than inhibition of AR—ligand interaction. To demonstrate that ARΔLBD has ligand-independent AR function and is a suitable target for identification of inhibitors, we experimentally generated CWR22R cells in which only ARΔLBD is present. CWR22R cells were co-transduced with shRNA targeting the untranslated region of the endogenous AR transcript and an expression construct directing ectopic expression of ARΔLBD (FIG. 1). In these cells, the ARΔLBD mutant is constitutively active as a transcription factor and is localized to the nucleus even in the absence of any ligands (i.e., in steroid-free medium (SFM) made with charcoal-stripped serum FIGS. 1A and B). We also demonstrated that while elimination of all AR protein is toxic for CWR22R cells, ectopically expressed ARΔLBD can support proliferation of CWR22R cells in the absence of full length AR (FIG. 1C-E). These results indicate that the ARΔLBD mutant form of AR has the same transcriptional and pro-survival activity as the full length protein, but without the requirement for ligand.

In order to monitor the effect of library chemicals on an activity of AR, we introduced an AR-dependent luciferase reporter construct (pARE-Luc) into CWR22R cells to generate a stable cell line with an integrated reporter. A library of 34,000 small molecules was applied at a concentration of 20 µM to the resulting CWR22R-ARE-Luc cells and compounds that inhibited luciferase activity in the reporter cells at least two-fold after 24 hrs incubation were selected as primary hits. From the list of primary hits we excluded (i) compounds inhibiting other reporter systems tested with the same library (e.g., CMV-GFP, E-box-luciferase) to avoid general or non-specific inhibitors of transcription or translation and inhibitors of luciferase enzymatic activity, and (ii) compounds toxic to non-PCa cells (e.g., HeLa, melanoma, RCC cells) to avoid non-specific (clearly unrelated to AR signaling) toxic compounds. Filtered hits were confirmed in a reporter dose response assay using CWR22R-ARE-Luc cells and those with an $EC_{50}$ (effective concentration resulting in reduction of reporter activity by 50%) of <10 µM were selected for further analysis.

To confirm the AR-inhibitory activity of hits on an endogenous AR target gene, we assessed the effect of compounds on Prostate Specific Antigen (PSA) expression. This assay was performed in a different PCa cell line (C4-2) than that used for library screening in order to exclude hits specific for one particular cell type. The C4-2 cell line is a derivative of the androgen-sensitive LNCaP cell line that was selected based on its ability to grow in castrated mice and, therefore, presents another model of castration resistant PCa. C4-2 cells have the same AR LBD mutations as LNCaP cells but have altered AR co-regulators expression, which make AR several fold more sensitive to DHT. Compounds that inhibited PSA secretion by C4-2 cells by >60% when applied at a concentration of 10 µM were selected for further analysis using luciferase activity in CWR22R-ARE-Luc cells incubated for 24 h in the presence of 10 µM of compounds and analyzed as a percentage of luciferase activity in cells incubated with 0.1% DMSO. The effect of shAR6 was measured at 72 h; the level of PSA in the medium of C4-2 cells incubated for 72 h in the presence of 10 µM of compounds was analyzed as a percentage of the PSA level in cells incubated with 0.1% DMSO. The effect of shAR6 was measured at 72 h. The number of colonies grown in the presence of 10 µM of compounds was analyzed as a percentage of colony formation in the presence of 0.1% DMSO.

Selected compounds inhibited AR transcriptional activity in both cell lines (CWR22R and C4-2) in the presence of steroids naturally present in FBS or in the presence of up to 10 nM dihydrotestosterone (DHT) in SFM. Therefore, the selected compounds are inhibitors of AR transcriptional activity in at least two models of androgen-independent PCa.

EXAMPLE 3

Figure 2:
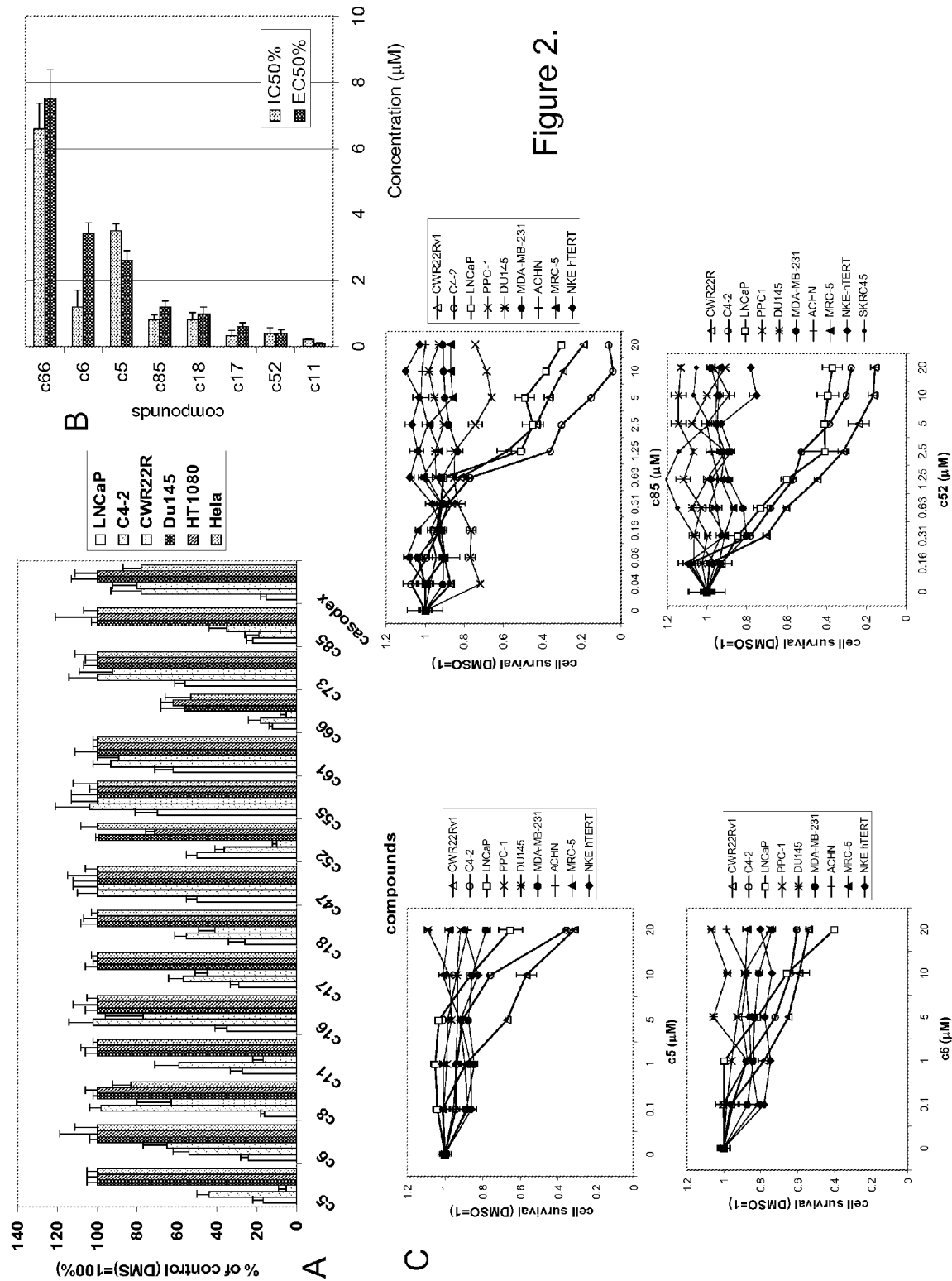
FIG. 2A-2C depict data showing toxicity of AR inhibitors to different cells.

This Example provides a description of the effect of the selected compounds on the growth of PCa cells. To test the toxicity of the identified AR inhibitors towards cells of different origins, we performed colony formation assays using a single dose of each compound (10 µM) on several PCa (LNCaP, C4-2, CWR22R and DU145) and two non-PCa (HT1080 and HeLa) cell lines (FIG. 2A). With the exception of a single compound (c66), the selected small molecules did not affect the growth of non-PCa cells or AR-negative PCa cells (DU145). Almost all of the molecules tested, as well as the positive control bicalutamide (an AR inhibitor currently used in the clinic), suppressed growth of AR-expressing androgen-sensitive LNCaP cells to different degrees (FIG. 2A). At the same time, bicalutamide did not suppress growth of either C4-2 or CWR22R cells (AR-expressing, androgen-independent cell lines), while some of the selected molecules did. Thus, we identified several compounds (c5, c6, c11, c17, c18, c52, c85) with different degrees of toxicity towards three AR-expressing PCa cell lines but no toxicity towards non-PCa cells or AR-negative cells. However, several compounds (c8, c16, c47, c55, c61, c73) behaved similarly to bicalutamide in that they suppressed growth of LNCaP cells, but not CWR22R or C4-2 cells. These compounds were not weaker inhibitors of AR transcriptional activity in CWR22R or C4-2 cells than compounds that inhibited growth of the cells. For example, compounds c55, c61 and c85 are comparable inhibitors of AR-dependent transcription as judged by $EC_{50}$ and maximal inhibition of ARE-Luc reporter activity and PSA secretion; however, while c85 inhibits growth of the androgen-independent CWR22R and C4-2 cell lines, c55 and c61 do not. These findings demonstrate that inhibition of AR-dependent transcriptional activity is not, in itself, sufficient to suppress growth of androgen-independent PCa cells.

Our finding that the parameter used in the library screening, inhibition of AR-dependent reporter expression in CWR22R cells, does not necessarily reflect the toxicity of compounds to these cells suggests two possible explanations: (i) AR controls survival of androgen-independent PCa cells through a transcription-independent mechanism and the pool of identified compounds that inhibit AR-dependent transcription includes some compounds that also inhibit the postulated transcription-independent anti-apoptotic function of AR; or (ii) the toxicity of the AR inhibitors identified in the screen is independent of AR and the observed inhibition of AR transcriptional activity is a reflection of toxicity or other effects of these compounds occurring through some other mechanism. The fact that the toxic compounds identified in our screen display specificity in their toxicity (toxic to three of three tested target PCa cell lines expressing AR, but not toxic to three of three tested non-target cell lines) argues against the second scenario.

To further analyze the AR-specificity of the compounds, we compared quantitative parameters of AR inhibition and PCa cell toxicity caused by the compounds. $EC_{50}$ for inhibition of AR-dependent luciferase activity in CWR22R cells measured 24 h after compound addition was compared to $IC_{50}$ for toxicity against CWR22R cells (inhibitory concentration of compound resulting in 50% fewer viable cells) 6 days after compound addition (FIG. 2B). Importantly, none of the compounds demonstrated toxicity at 24 h (data not shown). This is similar to the delayed toxic effect of AR-targeting siRNA on these cells, which becomes apparent 4-6 days after application of the siRNA. FIG. 2B shows that the $EC_{50}$ for inhibition of the AR-dependent reporter at 24 h is within the same range as the $IC_{50}$ for toxicity at 6 days. This demonstrates that inhibition of AR-dependent transcription occurs before toxicity and that there is a correlation between AR inhibition and toxicity to PCa cells for those compounds that are toxic to PCa cells. These results, together with the fact that some AR inhibitors are not toxic, suggests that there are different modes by which AR can be inactivated: (i) inhibition of only the transcriptional activity of AR is not toxic for androgen-independent PCa cells (similar to the effect of androgen withdrawal); (ii) inhibition of AR transcriptional activity together with some other transcription-independent function of AR that controls survival of PCa cells is toxic to both androgen-dependent and -independent PCa cells; and (iii) inhibition of only the postulated transcription-independent pro-survival function of AR without affecting AR-mediated transcription would be expected to be toxic to all PCa cells, although such inhibitors were not identified so far. Our readout system was based on monitoring AR-dependent transactivation, and compounds acting through the hypothetical third mode were not be isolated in our screen.

We also tested the effect of the selected compounds on a larger group (n=10) of non-target cell lines (non-PCa cell lines and PCa cells that do not express AR). Examples of these data are shown in FIG. 2C. Selected hits were toxic only to target cells and non-toxic to AR-negative cells at all concentrations tested. Thus, we can conclude with a high level of confidence that the selected hits that display toxicity are toxic only to PCa cells expressing AR; and therefore, the toxicity of these compounds is likely to be related to their effect on AR.

Figure 3:
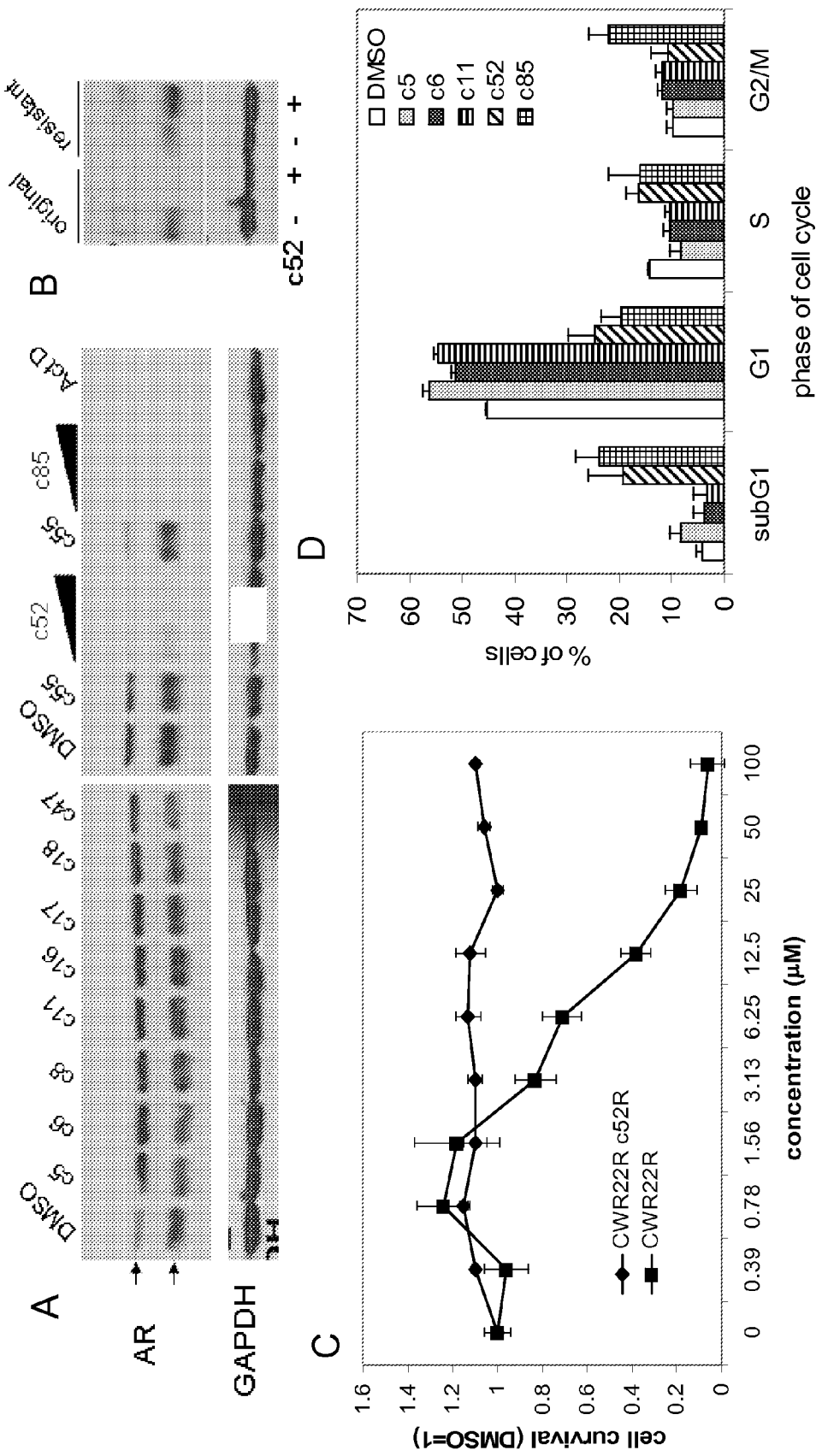
FIGS. 3A-3D depict data showing a that reduction of AR protein levels is associated with toxicity of the selected AR inhibitor hits to PCa cells.

The data in FIG. 2C also show that the compounds that are toxic to PCa cells can be divided into two categories based on the degree of their toxicity: compounds c52 and c85 kill practically all of the PCa cells in the culture by day 7; in contrast, other compounds caused reduced growth as compared to untreated control cells, but not obvious cell death (FIG. 2C, compounds c5 and c6, and data not shown for compounds c11, c17, c18). In these latter cases, increasing the time of incubation or the dose of the compounds still did not result in complete elimination of the cells. This suggests that a subset of the compounds suppress proliferation of PCa cells, but do not kill them. To test this possibility, we assessed the cell cycle distribution of CWR22R cells treated with both categories of compounds. Treatment with compounds of the first type (c52, c85) leads to the appearance of cells with sub-G1 DNA content characteristic of apoptotic cells (FIG. 3D). In contrast, treatment of the cells with representative compounds of the second type (c5, c6, c11) did not result in appearance of cells with sub-G1 DNA content, but did lead to changes in cell cycle distribution indicative of cell cycle arrest (an increase in the proportion of cells in the G1 phase of the cell cycle and a decrease in the proportion of cells in S phase). Therefore, different subsets of compounds inhibiting AR-dependent transcription in androgen-independent PCa cells cause either growth arrest or apoptosis in these cells. Whether a compound causes growth arrest or apoptosis is not determined by the potency of the compound as an inhibitor of AR-dependent transcription (i.e., FIG. 2B).

EXAMPLE 4

This Example provides a description of the correlation between the toxicity of compounds towards PCa cells and their effect on AR protein levels.

Based on the results described above, we can distinguish three categories of compounds among the inhibitors of AR-dependent transcription identified in our screen: (i) bicalutamide-like compounds that suppress growth of androgen-sensitive LNCaP cells but do not affect growth of androgen-independent C4-2 or CWR22R cells (c8, c16, c47, c55, c61, and c73); (ii) compounds that suppress growth of all (both androgen-dependent and -independent) PCa cells expressing AR (c5, c6, c11, c17, and c18); and (iii) compounds that kill all PCa cells expressing AR (c52 and c85). The AR inhibitors in the first category likely target ligand binding (meaning they are not toxic to androgen independent cancer cells) and thus are not considered to be useful in the method of the invention. The other two categories were of interest as they appeared to represent new types of AR inhibitors for potential treatment of androgen-independent PCa and other AR positive cancers, and the are therefore termed ARTIS (AR Transcription Inhibitors—Suppressive, including compounds c5, c6, c11, c17, c18) and ARTIK (AR Transcription Inhibitors—Killing, including compounds c52 and c85).

In an effort to elucidate why ARTIS and ARTIK compounds have different effects on the growth of PCa cells, we compared AR protein levels in CWR22R cells treated with both categories of compounds as well as several hits of the first category that are not toxic to PCa cells. This analysis showed that treatment with ARTIKs (c52 and c85) led to complete disappearance of AR protein from the cells. In contrast, treatment with ARTIS compounds or non-toxic AR inhibitors did not affect the level of AR protein in the cells (FIG. 3A). This supports that AR controls survival of androgen-independent PCa cells through a transcription-independent mechanism. Comparison of the various compounds indicates that elimination of AR protein leads to death of androgen-dependent and -independent cells (and would account for the observed inhibition of AR-dependent transcription). On the other hand, inhibition of AR-dependent transcription without a decrease in AR protein levels suppresses growth of androgen-dependent and, in some cases, androgen-independent PCa cells, but does not kill them. The critical importance of AR elimination for the toxic effect of one ARTIK compound was demonstrated by in vitro selection of a CWR22R clone resistant to ARTIK toxicity (FIG. 3B, see Example 1 for details). A single clone was obtained after growth of $10^7$ cells in the presence of c52 and this clone retained expression of AR even when grown in the constant presence of c52 (FIG. 3C), which indicates that AR is likely a direct target of c52. No clones resistant to compound c85 were obtained.

Figure 4:
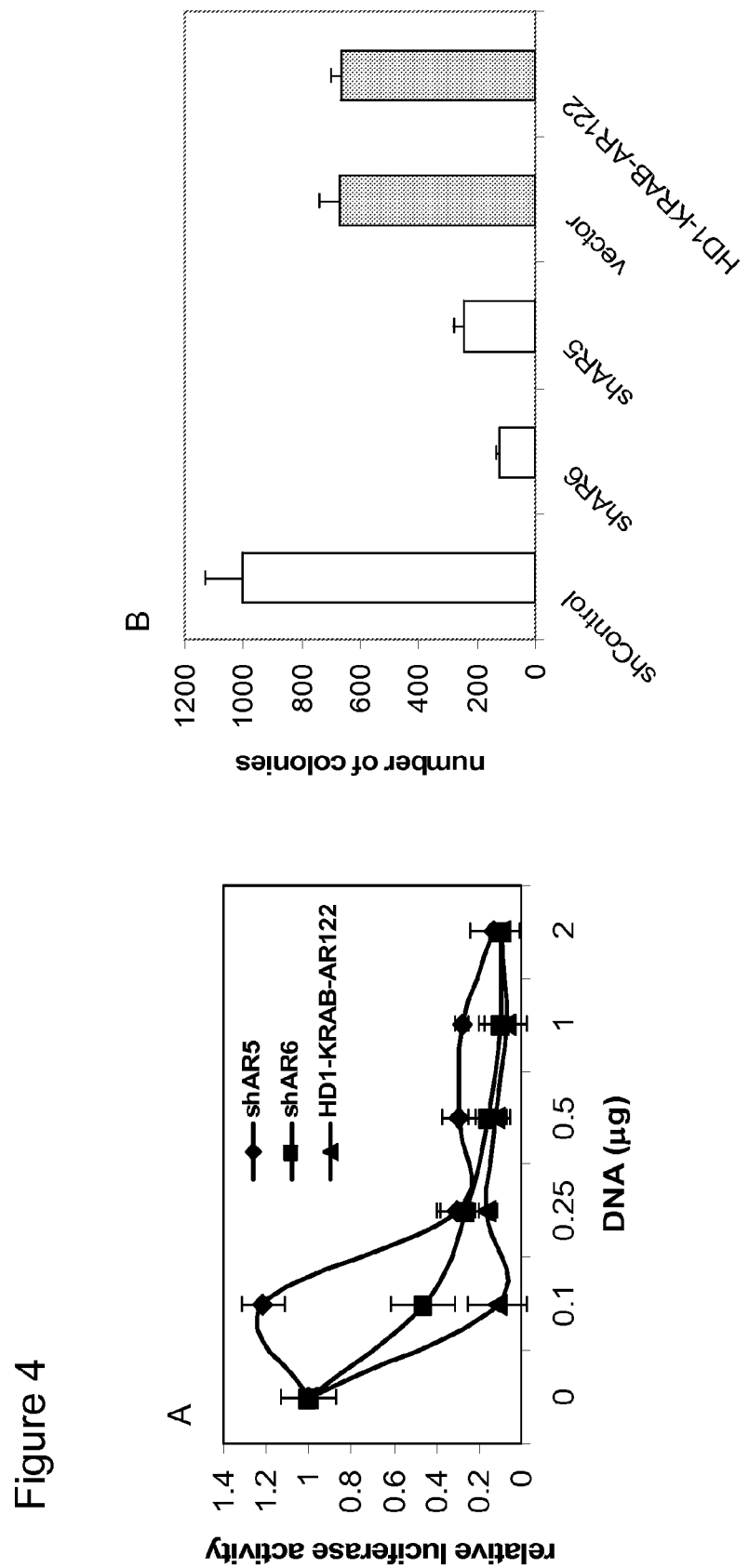
FIG. 4 provides a graphical representation of data obtained from conducting reporter assay on CWR22R cells cotransfected with pARE-Luc and different amounts of shRNA or AR mutant HD1-KRAB-AR122 constructs as shown on the x-axis. The total amount of DNA in the transfection mixture was kept equal by adding shControl vector DNA. Transfection efficiency was normalized by cotransfection of pCMV-b-gal construct. Assays were run in duplicate.

As an additional test of whether a transcription-independent function of AR controls survival of PCa cells, we compared the effects of two gene constructs on the survival of CWR22R cells. ShRNA targeting AR causes suppression of AR expression leading to elimination of AR protein similar to ARTIK compounds). On the other hand, the AR mutant, HD1-KRAB-AR122, in which part of the AR transactivation domain (aa 1-122) is substituted with the transrepression domains of KRAB and HDAC1, does not affect endogenous AR protein levels, but completely abolishes AR-dependent transcription by competing with endogenous AR protein for binding to ARE DNA sequences (Bramlett, et al. 2001. Mol Cell Endocrinol 183:19-28). These two constructs were tested for their effect on AR-dependent transcription over a range of doses in CWR22R cotransfection assays with the ARE-Luc reporter (FIG. 4A) and for their effect on CWR22R survival in colony formation assays (FIG. 4B). Both constructs almost completely suppressed AR-dependent luciferase expression in CWR22R cells, with the HD1-KRAB-AR122 mutant being slightly more potent than shRNA constructs upon transfection of an equal amount of DNA. However, as shown previously, shRNAs against AR suppressed growth of CWR22R colonies, while the HD1-KRAB-AR122 construct did not. This situation mimics that observed with our panel of AR inhibitory small molecules and provides additional support for the hypothesis that AR controls survival of PCa cells through a transactivation-independent function that has not been characterized previously.

EXAMPLE 5

Several steroid receptors (SR) are highly homologous, including AR, and the estrogen (ER), progesterone (PR), glucocorticoid (GR) and mineralcorticoid (MR) receptors. The ligand-activated forms of these receptors all recognize and bind to the same DNA sequence element. Attempts to isolate AR-inhibitory compounds acting downstream of receptor-ligand interaction (such as our screen) could, in theory, lead to isolation of molecules capable of inhibiting all of these SR Inhibition of ER or PR is not expected to be a serious problem for PCa treatment, since these receptors do not control vital functions in men. However, the GR and MR systems are functional in men and their inhibition by a cross-reactive AR inhibitor could cause adverse side effects, especially with chronic administration.

To determine whether any of our AR-inhibitory compounds also inhibit GR or MR, we first tested whether the CWR22RARE-Luc reporter system used for our screen is responsive to steroids other than androgens. This was an important experiment to perform since our library screen was done in the presence of FBS which might contain ligands of GR and MR. We treated CWR22RARE-Luc cells in SFM with either the GR ligand dexamethasone (Dex) or the MR ligand aldosterone (Ald) and measured luciferase activity in the presence or absence of the selected hits. Both Dex and Ald induced activity of the ARE-Luc reporter in CWR22R cells. Moreover, all selected AR-inhibitory hits suppressed this activity and the extent of suppression was proportional to their effect on DHT-induced ARE-Luc activity (data not shown).

Figure 5:
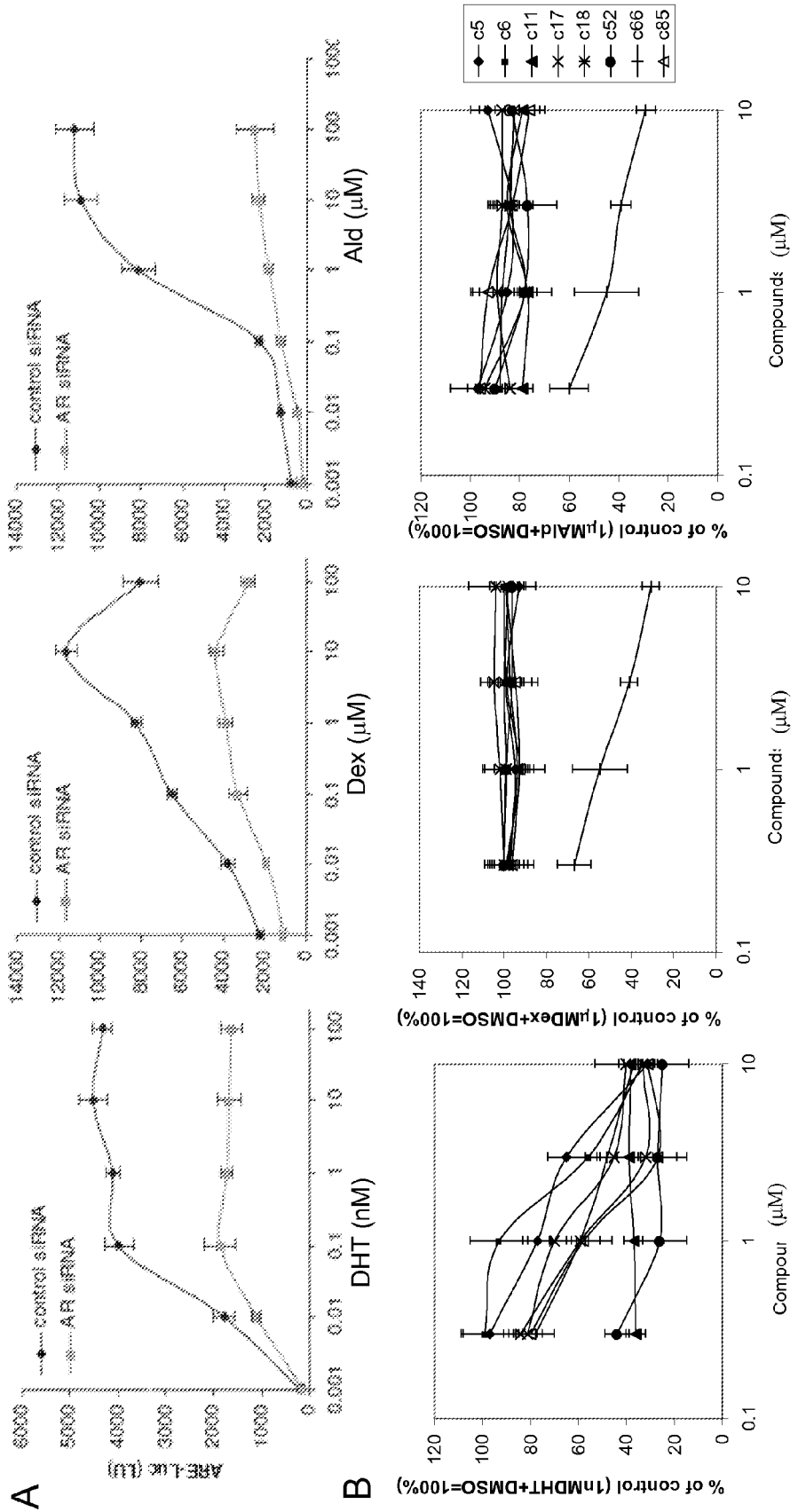
FIGS. 5A and 5B provides data showing the effect of AR inhibitors on the activity of steroid receptors.

CWR22R cells express not only ARΔLBD, but also full length AR containing LBD mutations that could affect its ligand specificity (FIG. 1). To test whether the observed induction of luciferase by Dex and Ald is due to activation of AR by these ligands, we used an AR-specific siRNA to block AR (both ΔLBD and full length) expression in CWR22R cells. ARE-Luc activation by all three ligands, DHT, Dex and Ald, was suppressed in these cells as compared to cells transfected with a control siRNA, which illustrates the promiscuous nature of the LBD-mutated AR present in CWR22R cells (FIG. 5A). This experiment demonstrated that the selected hits are able to inhibit AR even if it is stimulated by ligands other than DHT. At the same time, the data do not completely exclude the possibility that the hits affect GR and/or MR activity in other cells.

To further clarify whether our AR-inhibitory hits affect other SR, we used MDA-MB-453 breast cancer cells which, according to the literature, express GR, MR and AR (Zhou, Cet al. 2008. DBr J Pharmacol 154:440-45029). We transfected these cells with an MMTV-Luc reporter construct containing a DNA binding element recognized by all three SR in its promoter region. In this system, all hit compounds except for c66 were specific inhibitors of DHT-stimulated reporter activity, with no effect on Dex- or Ald-stimulated MMTV-Luc (FIG. 5B). Therefore, we conclude that most of the selected hit molecules are specific AR inhibitors that do not have activity even against the highly homologous GR and MR (Table 1).

EXAMPLE 6

Five hit compounds, representing both the ARTIS and ARTIK categories (c6, c11, c17, c52 and c85), were selected for in vivo tests based on all of the previous assays. Compound c5 was rejected due to very low microsomal stability (<5% after 1 hour incubation with rat microsomes). The toxicity of the compounds was evaluated in a dose escalation assay in which male NIH Swiss mice (n=4) received three sequential intraperitoneal (i.p.) injections of each compound delivered in 3 day intervals. The first dose was 20-fold higher than the in vitro $IC_{50}$ ($20 \times IC_{50}$) for the compound in CWR22R cells recalculated based on mouse weight (see Example 1) and the second and third doses were $50 \times IC_{50}$ and $100 \times IC_{50}$, respectively. On the day after the last injection, half of the mice in each group were sacrificed for gross pathology examination and collection of blood for serum biochemistry assays, which include total protein, glucose, bilirubin, and creatinine levels, activity of liver enzymes, and ion concentrations. The remaining mice were sacrificed and evaluated similarly 7 days after the last compound injection. No abnormalities were observed in any of the compound-injected mice upon either visual inspection of live mice or gross pathology examination. A minor decrease in serum glucose concentration (70-80% of control) was observed on the day after the last compound injection in almost all mice, but glucose levels were normal a week later (data not shown). Low serum glucose level might reflect of a weak transient GR-inhibitory effect of the selected compounds. Overall, however, this experiment demonstrated that the tested doses of compounds are non-toxic in mice and therefore suitable for in vivo efficacy testing.

Figure 6:
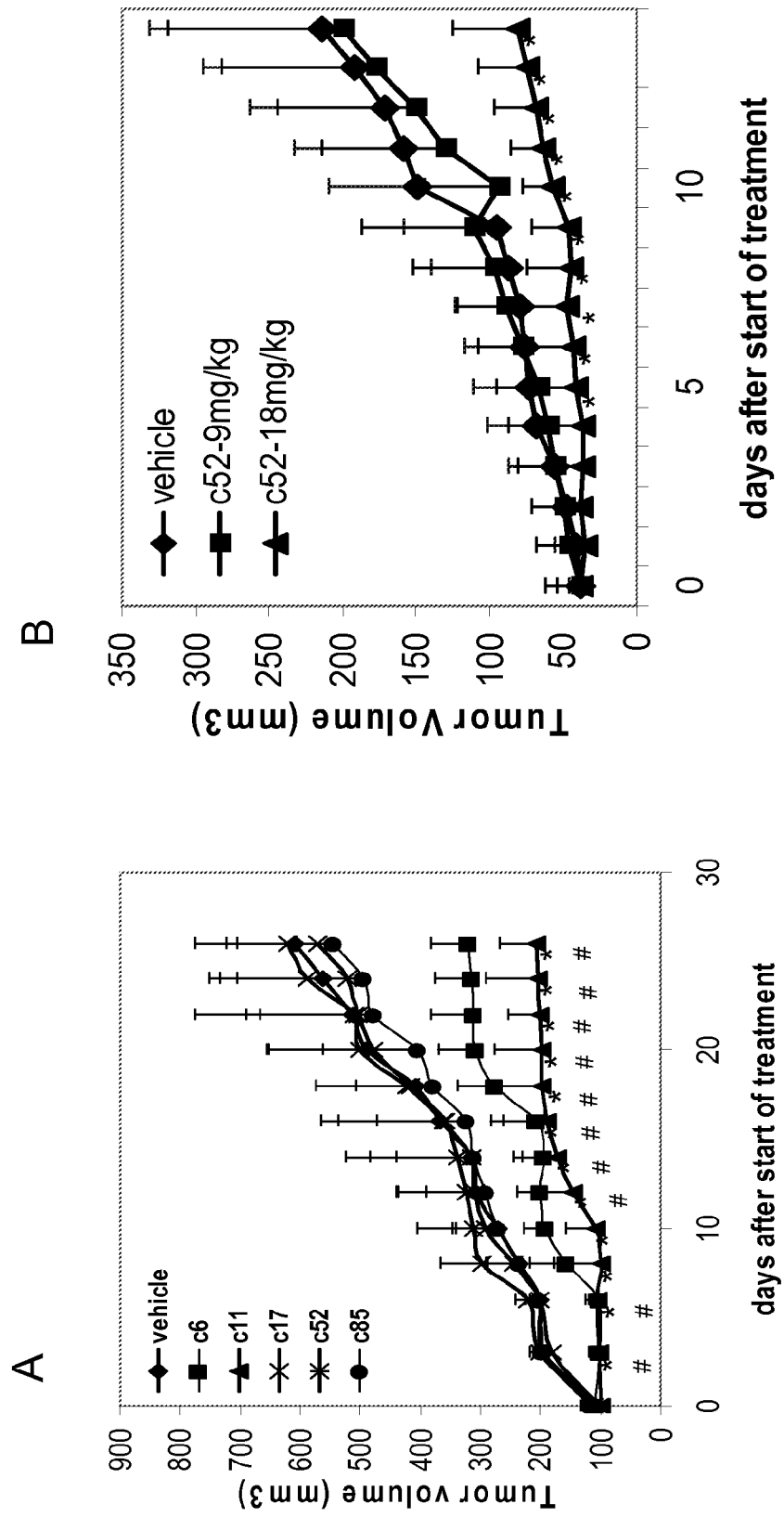
FIGS. 6A and 6B provide data showing anti-tumor activity of the selected hits in mouse models of androgen-independent PCa.

We evaluated the potential anti-tumor effect of the hits using C4-2 and CWR22R xenograft models of androgen-independent PCa in nude mice. Groups of C4-2 tumor-bearing mice (4-5 mice per group, each with two tumors) were given 6 daily i.p. injections of compound ($100 \times IC_{50}$ dose) or DMSO vehicle. Under this treatment regimen, compounds c6 and c11 demonstrated clear suppression of C4-2 tumor growth, while c17, c52 and c85 did not (FIG. 6A).

ARTIK compounds, c52 and c85, were also tested in the CWR22R model. Five daily intravenous (i.v.) injections of c52 at a dose of 18 mg/kg/day (equivalent to $200 \times IC_{50}$) suppressed growth of subcutaneous CWR22R tumors (FIG. 6B) without any noticeable adverse side effects. Compound c85 did not demonstrate reliable suppression of tumor growth. Among 10 mice treated with 18 mg/kg/day of c52, tumors completely disappeared in 2 mice, regressed in 1 mouse and did not grow in size in 5 mice. In contrast, 9 out of 10 control animals displayed progressively growing tumors and 1 mouse had a slowly growing tumor.

These in vivo results indicate that representatives of both ARTIK and ARTIS (compounds c6, c11 and c52) are generally non-toxic, yet block growth of androgen-independent PCa tumors and, therefore, have potential as candidate therapeutic agents against PCa and AR positive BC. Given the benefit of the present disclosure, it is likely that routine experimentation could be used for pharmacological optimization to significantly improve the anti-tumor efficacy of these compounds as well as reveal in vivo efficacy of other hit compounds that did not suppress tumor growth in these experiments.

EXAMPLE 7

This Example presents an analysis of the effects of compounds against AR positive and AR negative cancer cells, as well as non-cancerous cells. In particular, the compounds were tested against AR positive breast cancer cells, AR negative breast cancer cells, AR positive prostate cancer cells, AR negative renal cell carcinoma, AR negative cervical cells, and AR positive hepatocarcinoma and normal hepatocytes. The experiments described in this Example were performed essentially as described in Example 1. The results demonstrate that compounds described herein as suitable for use in the method of the invention are effective in inhibiting growth of AR positive cancer cells, but not AR negative cancer cells. The results are graphically summarized in FIGS. 12-20.

It will be clear to those skilled in the art from the foregoing description of the invention and the Examples that, in order to identify new types of AR inhibitors that for use in treatment of androgen-independent (and androgen dependent) PCa, we screened small molecules against a form of AR lacking the LBD (ARΔLBD). Targeting of other AR domains is less likely to result in selection of mutations leading to relapse, since most mutations would be expected to result in loss of domain function (e.g., transactivation, DNA binding, cofactor interaction).

A number of our findings demonstrated that ARΔLBD is completely androgen-independent, yet retains all AR functions essential for PCa cell viability: i) it activates expression of the pARE-Luc reporter from the AR-specific probasin promoter (see Example 1), ii) while CWR22R cells cannot survive in the absence of AR, expression of ARΔLBD is sufficient to support normal proliferation of these cells, and iii) the activity of ARΔLBD in SFM is equal or superior to that of wild type AR in the presence of androgens (in assays of reporter activity, nuclear localization, etc). These data validate use of ARΔLBD as a target for identification of new types (not affecting ligand binding) of AR inhibitors capable of interfering with the functions of AR critical for cell survival and having broad activity against different variants of AR.

The approach that we took to target AR was based on a different rationale and utilized different strategies than other reports describe. Attar et al. reported rational design of new non-steroidal AR inhibitors based on resolution of the crystal structure of bicalutamide bound to the LBD of AR (Salvati, et al. 2005. *Bioorg Med Chem Lett* 15:271-276). These new inhibitors have improved AR-binding properties as compared to bicalutamide and, while bicalutamide is active against some mutant forms of AR, the new compounds are more toxic to androgen-independent PCa cells. Nevertheless, this approach is a variant of therapy targeted against the AR LBD and is therefore likely to be limited by the mutability of the LBD.

Another group found that upon selection of androgen-sensitive LNCaP cells for the ability to grow in the absence of androgens, the most prevalent genetic change was amplification of the AR gene Nat Med 10:33-39). The authors postulated that the observed amplification was selected since it compensated for the low activity of AR in the absence of ligand by augmenting the number of AR molecules per cell. The same group recently reported that they used these cells to select a small molecule with activity against androgen-independent PCa (Tran, et al. 2009. Development of a second-generation antiandrogen for treatment of advanced prostate cancer. Science 324:787-790). This molecule, MDV3100, has demonstrated efficacy in decreasing PSA levels in a Phase I clinical trial in patients with castration resistant PCa. However, the mechanism of activity of MDV3100 against AR is different from what we believe the AR inhibitors isolated by our approach use. MDV3100, as well as its close homologue RD 162, are both non-competitive antagonists of AR that bind with high affinity to the AR LBD. The binding affinity of MDV3100 (and RD162) is the closest to that of androgen that has been achieved so far for an antagonist. Thus, these compounds prevent activation of AR by androgens with superior potency as compared to the AR antagonists available in the clinic, such as bicalutamide and flutamide. In addition, the latter molecules are hampered by a partial agonist activity which is not displayed by MDV3100 or RD162 (Tran, et al. 2009. Development of a second-generation antiandrogen for treatment of advanced prostate cancer. *Science* 324:787-790). Potential problem with these new compounds may come from the fact they also bind LBD and may induce selection of mutations in LBD as casodex does.

One of the unexpected findings of our screen was that loss of AR transcriptional activity does not necessarily lead to inhibition of growth or survival of androgen-independent PCa cells. Almost all of the molecules that we identified as inhibitors of AR-dependent transcription also inhibited growth of LNCaP cells, thereby confirming that AR transcriptional activity is important for growth of ligand-dependent PCa cells. However, only some compounds had an effect on growth of androgen-independent PCa cells (C4-2 and CWR22R). Importantly, the few hit compounds that did suppress growth of all PCa cells expressing AR (both androgen-dependent and -independent) were not necessarily more potent as inhibitors of AR-dependent transcription than molecules showing no effect on growth of androgen-independent PCa cells. Significant proportion of non-toxic versus toxic (causing death or growth arrest) inhibitors of AR-dependent transcription in the screen results indicates that inhibition of AR-dependent transcription does not solely determine toxicity, at least for androgen-independent PCa cells. This suggests that another, so far uncharacterized, function of AR besides transcriptional regulation is important for survival of PCa cells. These results also suggest that the transcriptional regulation function of AR can be inhibited specifically using small molecules without elimination of this other postulated pro-survival function.

Further characterization of the AR-inhibitory hits displaying toxicity against androgen-independent PCa showed that they could be clearly separated into two categories, those that kill PCa cells and those that only suppress their proliferation. In addition, the effect of the compounds on AR protein levels correlated with the type of toxicity that they induced: compounds causing elimination of AR protein killed androgen-independent PCa cells while compounds having no effect on AR levels only suppressed their growth. This data again may be explained by the presence of a transcription-independent function of AR that controls survival of PCa cells and is only completely abolished when AR protein is eliminated from the cells.

The idea that elimination of AR protein, not just inhibition of its transactivation function, is required to induce prostate cancer cell death is supported by the different effects of castration on normal prostate epithelial cells expressing wild type AR as compared to prostate tumor cells expressing AR with mutations in the LBD. Wild type AR is unstable in the absence of androgen, particularly if its binding partner HSP90 is limited. Thus, castration results in loss of AR protein and apoptosis in normal prostate epithelial cells. In contrast, since AR LBD mutations not only affect the specificity of ligand binding but also promote stability of AR in the absence of androgens, castration does not kill many PCa cells with mutated LBD, but only suppresses their proliferation.

The existence of a transcription-independent role of AR that controls survival of PCa cells is further supported by our finding that shRNA-mediated elimination of AR reduced colony formation by PCa cells while expression of the transactivation-deficient dominant negative HD1-KRAB-AR122 AR mutant did not. Thus, our data support the potential for AR to have a previously unrecognized transcription-independent function that impacts prostate cell survival It is notable that while some of our selected AR-inhibitory hits efficiently kill PCa cells and others have a weaker antiproliferative effect, compounds from both categories demonstrated efficacy against PCa tumor models in mice. The in vivo anti-tumor efficacy of compounds in both categories may be explained in several ways: (i) compounds undergo in vivo metabolic conversion which makes them more potent in vivo than in vitro; (ii) compounds have a mechanism of activity that is not crucial for PCa cell survival in vitro, but is much more important in vivo; and/or (iii) the growth suppressive effect of some compounds is sufficient to stop tumor growth in vivo.

A number of compounds that were toxic to androgen-independent PCa cells in vitro did not have any noticeable effect on in vivo tumor growth in the mouse models that we examined. Two potential explanations for this are: (i) these compounds have not been pharmacologically optimized, but could be based on the present disclosure without undue experimentation; and/or (ii) the mechanism of action of these compounds is not as important in vivo as in vitro. Compound C52 did not show in vivo efficacy in our experiment with the C4-2 model, but was effective in our experiment with CWR22R tumors. This difference may be due to our use of a higher compound dose and different route of administion (i.v. versus i.p.) in the latter experiment. Intravenous injection could significantly improve the bioavailability of relatively unstable compounds such as c52 (17% of compound left after 1 h incubation with rat microsomes) by avoiding the first pass through the liver that occurs with i.p. injections. Thus, the lack of efficacy for c52 in the C4-2 model may be due topoor pharmacological properties of the compound which could be addressed based on the present disclosure by one skilled in the art.

In summary, we have identified a number of AR-inhibitory compounds with very specific anti-PCa properties in vitro and in vivo. These compounds represent a new class of AR inhibitors since they do not target AR-ligand interaction. Therefore, it is likely that they will be active against AR positive cells regardless of LBD mutations that develop in response to standard anti-androgen therapy. Thus, the chemical classes to which the particular compounds tested in the present disclosure belong are also expected to be useful against AR positive cancers.

We claim:

1. A method for inhibiting the growth of androgen receptor "AR" positive breast and prostate cancer cells in an individual having AR positive breast or prostate cancer comprising administering to the individual a composition comprising a compound selected from the group of compounds having the structures:

i)

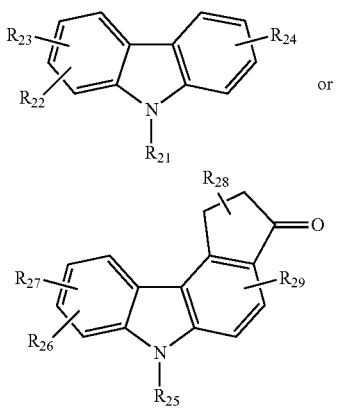

or wherein $R_{28}$=

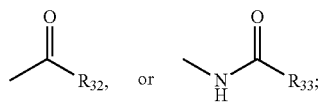

and wherein $R_{21}$ or $R_{25}$ is hydrogen or an alkyl group comprising 1 to 6 carbons, which is, optionally, substituted with one or more hydroxyl groups or cyano groups, wherein $R_{22}$, $R_{23}$ and $R_{24}$ or $R_{26}$, $R_{27}$ or $R_{29}$ are independently hydrogen, an alkyl group comprising 1 to 6 carbons, an alkyl ketone group, where the alkyl moiety comprises 1 to 4 carbons and is, optionally, substituted with one or more halides, halide, an alkyl sulfonamide, where the alkyl group comprises 1 to 4 carbons, a hydroxyl group, an alkoxy group, where the alkyl moiety comprises 1 to 4 carbons, or the following group:

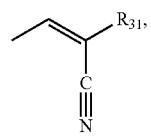

wherein $R_{31}$ is an alkyl group comprising 1 to 6 carbons, which is, optionally, substituted with one or more halides, or an amino group, wherein $R_{32}$ is an alkyl group comprising 1 to 6 carbons, which is, optionally, substituted with one or more halides, or an amino group, wherein $R_{33}$ is an alkyl group comprising 1 to 6 carbons, which is, optionally, substituted with one or more halides, an amino group, an alkylketone group comprising from 1 to 4 carbons, which is, optionally, substituted with one or more halides, or an alkylcyclohexyl group, where the alkyl moiety comprises 1 to 4 carbons;

ii)

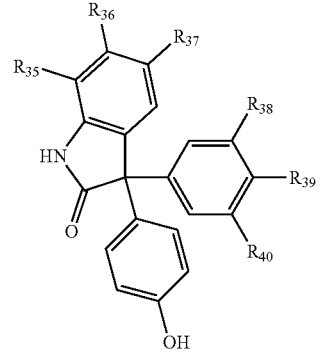

wherein $R_{35}$ is hydrogen, an alkyl group comprising 1 to 6 carbons, which is, optionally, substituted with one or more halides, or halide, wherein $R_{36}$ and $R_{37}$ are independently hydrogen or an alkyl group comprising 1 to 6 carbons, which is, optionally, substituted with one or more halides, wherein $R_{38}$ and $R_{39}$ are independently hydrogen or an alkyl group comprising 1 to 6 carbons, which is, optionally, substituted with one or more halides, or a hydroxyl group, and wherein $R_{40}$ is hydrogen or a hydroxyl group;

iii)

[Chemical structure]

wherein $R_1$=

[Chemical structures: substituted phenyl with $R_5$, $R_6$ or N-methylpiperidine with $R_7$]

wherein $R_4$=

[Chemical structures: substituted phenyl with $R_8$, $R_9$ or 5-membered ring with $X_1$ and $R_{10}$]

wherein $R_5$, $R_6$ and $R_7$ are independently hydrogen, an alkyl group comprising 1 to 6 carbons, an aryl alkyl group, where the aryl moiety comprises 5 or 6 carbons and the alkyl moiety comprises 1 to 4 carbons, an alkyl ketone group, where the alkyl moiety comprises 1 to 4 carbons, halide, or a hydroxyl group, wherein $R_3$ is hydrogen or hydroxyl group, wherein $R_8$, $R_9$ and $R_{10}$ are independently hydrogen, an alkyl group comprising 1 to 6 carbons, a halide, or a nitro group, and wherein $X_1$ is an oxygen atom or sulfur atom;

iv)

[Chemical structure: perimidine with $R_{11}$]

wherein $R_{11}$=

[Chemical structures: substituted phenyl with $R_{12}$, $R_{13}$, $R_{14}$ or 5-membered ring with $X_2$]

wherein $R_{12}$, $R_{13}$ and $R_{14}$ are independently hydrogen, an alkyl group comprising 1 to 6 carbons, an alkyl ether group, where the alkyl moiety comprises 1 to 6 carbons, halide, an amino group, a hydroxyl group, or a nitro group, and wherein $X_2$ is an oxygen atom or sulfur atom;

v)

[Chemical structure: 1,4-diaminobenzene with $R_{15}$ and $R_{16}$ acyl groups]

wherein $R_{15}$=

[Chemical structures: substituted phenyl with $R_{17}$, $R_{18}$ or benzodioxine]

wherein $R_{16}$=$C_1$-$C_6$ alkyl group or

[Chemical structure: substituted phenyl with $R_{19}$, $R_{20}$]

wherein $R_{17}$ and $R_{18}$ are independently hydrogen, an alkyl group comprising 1 to 6 carbons, or an alkyl ether group, where the alkyl moiety comprises 1 to 4 carbons, wherein $R_{19}$ and $R_{20}$ are independently hydrogen, an alkyl group comprising 1 to 6 carbons, or halide, and combinations of the compounds set out in i)-v);

wherein growth of the androgen receptor positive cancer in the individual is inhibited after administration of the composition to the individual.

2. The method of claim 1, wherein the compound has the following structure:

[Chemical structure: N-propyl carbazole with acetyl group]

3. The method of claim 1, wherein the compound has the following structure:

[Chemical structure: N-methyl indolinone with two hydroxyphenyl groups]

4. The method of claim 1, wherein the compound has the following structure:

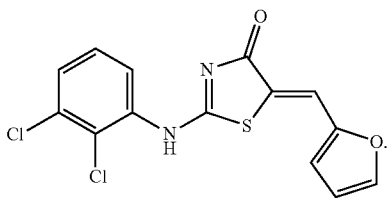 [SMILES: O=C1N=C(Nc2cccc(Cl)c2Cl)S/C1=C\c1ccco1]

5. The method of claim 1, wherein the compound has the following structure:

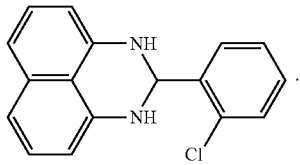 [SMILES: Clc1ccccc1C1Nc2cccc3cccc(c23)N1]

6. The method of claim 1, wherein the compound has the following structure:

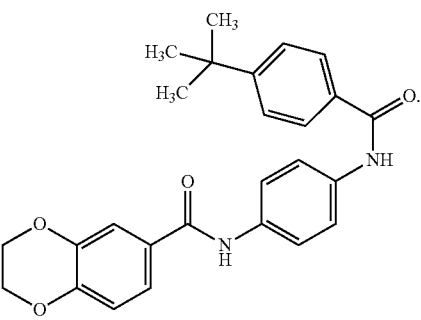 [SMILES: CC(C)(C)c1ccc(C(=O)Nc2ccc(NC(=O)c3ccc4c(c3)OCCO4)cc2)cc1]

7. The method of claim 1, wherein the individual is diagnosed with or suspected of having androgen receptor positive prostate cancer.

8. The method of claim 7, wherein the androgen receptor positive prostate cancer is androgen independent prostate cancer.

9. The method of claim 1, wherein the individual is diagnosed with or suspected of having androgen receptor positive breast cancer.

* * * * *